(12) United States Patent
Takita

(10) Patent No.: US 12,070,401 B2
(45) Date of Patent: Aug. 27, 2024

(54) STENT DEVICE HAVING LOOPED INTERLOCKING REGIONS AND NON-LOOPED INTERLOCKING REGIONS

(71) Applicant: OLYMPUS CORPORATION, Tokyo (JP)

(72) Inventor: Ko Takita, Hachioji (JP)

(73) Assignee: Olympus Corporation, Tokyo (JP)

( * ) Notice: Subject to any disclaimer, the term of this patent is extended or adjusted under 35 U.S.C. 154(b) by 134 days.

(21) Appl. No.: 17/673,135

(22) Filed: Feb. 16, 2022

(65) Prior Publication Data

US 2022/0273473 A1    Sep. 1, 2022

Related U.S. Application Data

(60) Provisional application No. 63/154,181, filed on Feb. 26, 2021.

(51) Int. Cl.
*A61F 2/90* (2013.01)

(52) U.S. Cl.
CPC ...................... *A61F 2/90* (2013.01)

(58) Field of Classification Search
CPC .................. A61F 2002/828; A61F 2/86; A61F 2220/0025; A61F 2250/0018;

(Continued)

(56) References Cited

U.S. PATENT DOCUMENTS 6,221,100 B1    4/2001   Strecker
8,585,731 B2 *  11/2013  Abbate .............. A61B 17/3478
                                                 606/199

(Continued)

FOREIGN PATENT DOCUMENTS

WO      99/49812 A2   10/1999
WO      00/33769 A1    6/2000
WO   2020/194506 A1   10/2020

OTHER PUBLICATIONS

International Search Report dated Apr. 5, 2022, issued in corresponding International Patent Application No. PCT/JP2022/008077.

*Primary Examiner* — Ariana Zimbouski
*Assistant Examiner* — Jacob Lee Fincher
(74) *Attorney, Agent, or Firm* — Morgan, Lewis & Bockius LLP

(57)    ABSTRACT

Stent device having stent wires interlocking with each other in various ways is disclosed. In primary interlocking structures, the stent wires include a loop formed in a first stent wire through which the second stent wire is threaded. Additional loops can be included in the primary interlocking structures, on one or both of the two stent wires. Primary interlocking structures are positioned at peaks and valleys in the respective first and second stent wires. Secondary interlocking structures do not contain loop features in the interlocking structure, but rather include first and second stent wires engaged with each other by passing first stent wire over the second stent wire forming a hanging arrangement with, e.g., the peak of one of the stent wires located in the valley of the other stent wire. Including one or more primary interlocking structures minimizes or prevents axial shortening and provides flexibility to the stent device.

27 Claims, 17 Drawing Sheets

(58) Field of Classification Search
CPC ............... A61F 2250/0029; A61F 2/07; A61F 2002/072; A61F 2002/075; A61F 2/82; A61F 2002/821; A61F 2002/823; A61F 2002/826; A61F 2/848; A61F 2002/8483; A61F 2002/8486; A61F 2/852; A61F 2/856; A61F 2/88; A61F 2/90
See application file for complete search history.

(56) References Cited

U.S. PATENT DOCUMENTS

| | | |
|---|---|---|
| 2009/0177272 A1 | 7/2009 | Abbate et al. |
| 2012/0041550 A1* | 2/2012 | Salahieh ............... A61F 2/2418 623/2.36 |
| 2013/0226282 A1 | 8/2013 | Ahn et al. |

* cited by examiner

| | Type | | Description | Axial shortening | Bend |
|---|---|---|---|---|---|
| ① | One loop<br>No loop | | Simple composition | ☆ | ☆☆☆ |
| ② | Two loops (B)<br>No loop | | Even if the stent is reduced in diameter, the stent can prevent axial shortening. (See below) | | |
| ③ | Two loops (A)<br>No loop | | Same as above | | |
| ④ | One loop<br>One loop | | By preventing the loop from moving along the wire, the stent can prevent axial shortening. (See below) | | |
| ⑤ | Two loops<br>One loop | | Stents have both ③ and ④ effects. | | |
| ⑥ | Two loops<br>Two loops | | Same as above | ☆☆☆ | ☆☆ |

FIG. 8A

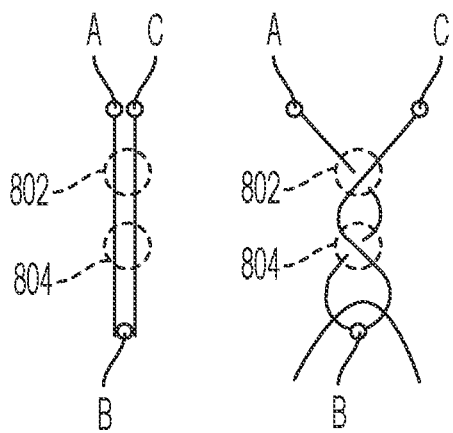

FIG. 8B

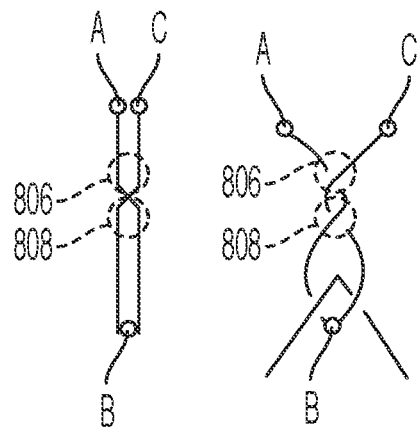

FIG. 8C

|   |   |   |
|---|---|---|
| Ⓐ | Size | |
| Ⓑ | Shape | |
| Ⓒ | Direction of rotation | |
| Ⓓ | Rise | |

STENT DEVICE HAVING LOOPED INTERLOCKING REGIONS AND NON-LOOPED INTERLOCKING REGIONS

RELATED APPLICATION DATA

This application is based on and claims priority under 35 U.S.C. § 119 to U.S. Provisional Application No. 63/154,181 filed on Feb. 26, 2021, the entire contents of which are incorporated herein by reference.

FIELD OF DISCLOSURE

The present invention relates generally to stent devices and, in particular, to a stent device having stent wires interlocking with each other so as to prevent axial shortening and gain flexibility of the stent device at an ideal proportion, particularly when the stent device is bent. The calculated placement of the interlockings of the stent wires provide variations of positive effects to the stent and the patient in whom the stent is placed.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

FIG. 20 is a figure of a stent device disclosed in the related art (U.S. Pat. Pub. No. 2013/0226282A1). FIG. 20 discloses the stent wires 100a, 100b, 100c, and 100d each having peaks 110a, 110b, 110c, and 110d and valleys 120a, 120b, 120c, and 120d. The peaks and valleys are occasionally "caught" by each other, for instance the peak 110b of the second stent wire 100b is caught by the valley 120a of the first stent wire 100a at location shown at 102. On the other hand, the peaks and valleys are occasionally "uncaught" by each other, for instance the peak 110b of the second stent wire 100b is uncaught by the valley 120a of the first stent wire 100a at location shown at 104. According to the related art, it is preferred that the number of the peaks 110 and the number of the valleys 120 be set to multiples of 3, such that the peaks 110 caught by the valleys 120 and the peaks 110 uncaught by the valleys 120 are repeated in a ratio of 2:1. It is possible to make the ratio 3:1 or 2:2 instead of 2:1, but there is a risk of damage to connected portions between the stent wires 100 when an external force is applied, since the number of the connected portions between the stents 100 is decreased. Therefore, it is preferable that the adjacent stent wires are interconnected in a repeated pattern in which first two consecutive peaks 110 of first stent wire are caught by first two consecutive valleys 120 of the adjacent stent wire and then one subsequent peak 110 of first stent wire is uncaught by one subsequent valley 120 of the adjacent stent wire, as illustrated in FIG. 18.

FIG. 21 is a figure of another stent device disclosed in the related art (U.S. Pat. No. 6,221,100). FIG. 21 discloses netting 11' having a mesh pattern where mesh 12' is formed with filaments 13' and 14' (the term "mesh" or "meshes" refers to the actual cord or wire network, and not the spaces therebetween). The points of intersection 15' of the filaments 13' and 14' form an eye 19 at every instance, where only one of the filaments is looped around the other filament. The radial bearing strength is increased by the eye 19, although the shortening of the stent by axial compression would not be possible due to the eye 19.

The drawback of the related art stent devices includes axial shortening of the stent device occurs due to axial compression after insertion into the human body. The axial shortening limits the range that the lumen of the stent device can be expanded within the human body. The drawbacks of the related art stent devices also include the inability of axial shortening and lack of flexibility of the stent device due to the eye formed at every intersection of the stent wires.

SUMMARY

Accordingly, there is a need for designing a stent device with an efficient structure in view of the practical usage, which would substantially obviate one or more of the issues due to limitations and disadvantages of related art stent device. An object of the present disclosure is to provide a stent device having an arrangement of looped interlocking regions and non-looped interlocking regions. The specific type of loop can vary and the non-looped interlocking regions contribute to ease of bending of the stent device and the looped interlocking regions contribute to prevent axial shortening when the stent device is bent. In a longitudinally direction of the stent device parallel to the longitudinal axis, i.e., in the axial direction, the looped interlocking regions can be arranged continuously or non-continuously. In other embodiments, the looped interlocking regions are continuous over two or more, alternatively two to four, sequentially arranged looped interlocking regions. Such improved stent devices have an efficient structure and provide practical administration of the associated medical procedure. At least one or some of the objectives is achieved by the stent device disclosed herein.

Additional features and advantages will be set forth in the description that follows, and in part will be apparent from the description, or may be learned by practice of the invention. The objectives and other advantages of the disclosed stent device will be realized and attained by the structure particularly pointed out in the written description and claims thereof, as well as the appended drawings.

Embodiments of the disclosed stent device comprises a first stent wire and a second stent wire forming a cylindrical stent body enclosing an interior void space and defines an inner luminal side of the stent body, a primary interlocking structure, and a secondary interlocking structure. The primary interlocking structure includes a first loop formed of the first stent wire and defining a first loop opening and the second stent wire passing through the first loop opening and the secondary interlocking structure includes the first stent wire and the second stent wire passing over each other. Furthermore, the first stent wire includes a first peak and a first valley and the first loop is located at the first peak or the first valley of the first stent wire.

Embodiments of the disclosed stent device further comprises the secondary interlocking structure not including a loop.

Embodiments of the disclosed stent device further comprises the secondary interlocking structure, the first stent wire, and the second stent wire pass over each without forming a loop.

Embodiments of the disclosed stent device further comprises the second stent wire including a second peak and a second valley, wherein a portion of the first stent wire forming the secondary interlocking structure is the first peak, wherein a portion of the second stent wire forming the secondary interlocking structure is the second valley, and wherein, in the secondary interlocking structure, the first peak is located in the second valley.

Embodiments of the disclosed stent device further comprises the primary interlocking structure including a second loop.

Embodiments of the disclosed stent device further comprises the second loop formed of the second stent wire and defines a second loop opening.

Embodiments of the disclosed stent device further comprises a portion of the second stent wire forming the second loop opening passes through the first loop opening.

Embodiments of the disclosed stent device further comprises the second loop formed at a peak or a valley in the second stent wire.

Embodiments of the disclosed stent device further comprises the second loop formed of the first stent wire and defines a second loop opening, and wherein the primary interlocking structure includes the second loop formed of the first stent wire.

Embodiments of the disclosed stent device further comprises the first loop and the second loop being part of a double-loop structure and wherein the first loop is the most distal of the first loop and the second loop.

Embodiments of the disclosed stent device further comprises the primary interlocking structure including a third loop.

Embodiments of the disclosed stent device further comprises the third loop formed of one of the first stent wire and the second stent wire and defines a third loop opening.

Embodiments of the disclosed stent device further comprises the primary interlocking structure including a fourth loop.

Embodiments of the disclosed stent device further comprises the fourth loop formed of one of the first stent wire and the second stent wire and defines a fourth loop opening.

Embodiments of the disclosed stent device further comprises the first loop, the second loop, the third loop and the fourth loop forming two double-loop structures.

Embodiments of the disclosed stent device further comprises a number of the primary interlocking structure being equal to or less than the number of the secondary interlocking structure.

Embodiments of the disclosed stent device further comprises a ratio of a number of the primary interlocking structure to a number of the secondary interlocking structure being 0.15 to 0.60, alternatively 0.15 to 0.40 or 0.15 to 0.30 or 0.25 to 0.40 or 0.40 to 0.60.

Embodiments of the disclosed stent device further comprises a stent cover, wherein the stent cover covers at least a portion of an outer circumferential surface of the cylindrical stent body.

Embodiments of the disclosed stent device further comprises a stent cover, wherein the stent cover covers at least a portion of an inner circumferential surface of the cylindrical stent body.

Embodiments of the disclosed stent device further comprises a stent cover, wherein a first portion of the stent cover covers at least a portion of an outer circumferential surface of the cylindrical stent body and wherein a second portion of the stent cover covers at least a portion of an inner circumferential surface of the cylindrical stent body.

Embodiments of the disclosed stent device further comprises the first stent wire not including three consecutive loops along the alternating peaks and valleys.

Embodiments of the disclosed stent device further comprises the first stent wire including one loop among the four consecutive alternating peaks and valleys.

Embodiments of the disclosed stent device further comprises the first stent wire including two loops among the four consecutive alternating peaks and valleys.

Embodiments of the disclosed stent device further comprises the two loops being consecutively placed along the alternating peaks and valleys.

Embodiments of the disclosed stent device further comprises the two loops being not consecutively placed along the alternating peaks and valleys.

Embodiments of the disclosed stent device further comprises the two loops interlocking with the second stent wire.

Embodiments of the disclosed stent device further comprises the first loop being asymmetric.

Embodiments of the disclosed stent device further comprises the first loop protruding outward as viewed from the inner lumen of the stent device.

Embodiments of the disclosed stent device further comprises the first stent wire and second stent wire being single wires.

Embodiments of the disclosed stent device further comprises a stent delivery system including a tip, a sheath having a capability to carry the stent device, and a pusher for pushing out the stent device from the sheath.

The term "patient," as used herein, comprises any and all organisms and includes the term "subject." A patient can be a human or an animal.

Other systems, methods, features and advantages will be, or will become, apparent to one with skill in the art upon examination of the following figures and detailed description. It is intended that all such additional systems, methods, features and advantages be included within this description, be within the scope of the present disclosure, and be protected by the following claims. Nothing in this section should be taken as a limitation on those claims. Further aspects and advantages are discussed below in conjunction with the embodiments of the disclosed input device. It is to be understood that both the foregoing general description and the following detailed description of the disclosed input device are examples and explanatory and are intended to provide further explanation of the disclosed stent device as claimed.

BRIEF DESCRIPTION OF THE DRAWING

The following detailed description of preferred embodiments can be read in connection with the accompanying drawings in which like numerals designate like elements and in which:

FIG. 8A is a table showing details of different types of loops and the relative ranking of each with respect to axial shortening and bending.

FIGS. 8B and 8D are schematic views showing embodiments of the structures of the interlocking portions of the stent wire.

FIG. 9 is a table showing details of factors that may affect the functions of each loops.

Figure 1:
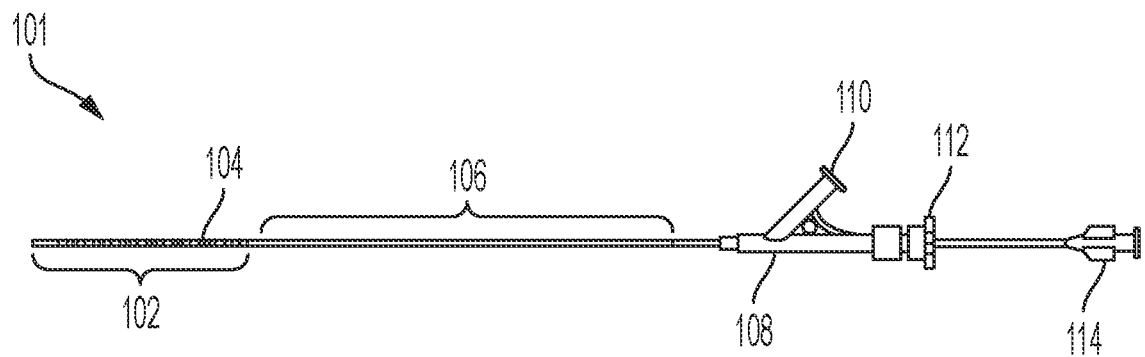
FIG. 1 shows an embodiment of a stent device delivery system with associated stent device.

Throughout all of the drawings, dimensions of respective constituent elements are appropriately adjusted for clarity. For ease of viewing, in some instances only some of the named features in the figures are labeled with reference numerals.

DETAILED DESCRIPTION

The following detailed description of preferred embodiments can be read in connection with the accompanying drawings in which like numerals designate like elements and in which: FIG. 1 is an illustration of a stent device delivering system 101. Stent delivery system 101 is comprised of tip portion 102, the stent device 104, sheath 106, two port hub 108, side port 110, rotatable handle lock 112, inner handle 114. The sheath 106 has a two-layered structure with inner sheath and outer sheath, having the stent device 104 in a reduced diameter held between the two layers at the tip portion 102. The tip portion 102 is connected to the inner sheath and the inner handle 114. The outer sheath is connected to the two port hub 108 and rotatable handle lock 112. After the stent delivery system 101 places the tip portion 102 and the stent device 104 to the desired position, by fixing the inner handle 110 and pulling the rotatable handle lock 112 toward the proximal side of the delivery system 101, the outer sheath at the tip portion 102 slides toward the proximal side, causing the stent device 104 to self-expand from the reduced diameter to the designed diameter. After the outer sheath finishes sliding the entire length of the stent device 104, the delivery system 101 and the stent device 104 are separated, leaving the stent device 104 to be implanted in the patient's body.

Figure 2A:
FIGS. 2A and 2B show schematic views of the stent device with the stent body in a collapsed state (FIG. 2A) and in an expanded state (FIG. 2B).
Figure 2B:
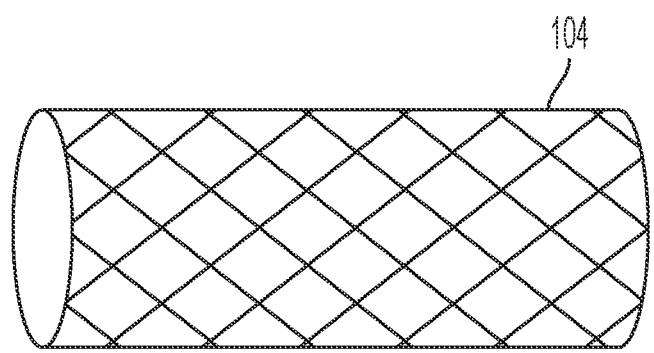

FIG. 2A is an illustration of the stent device 104 with the stent body in its contracted state. The extent of the axial shortening occurring as the stent body contracts is dependent on the interlocking structures of the stent wires. The stent device 104 is inserted into the stent delivery system 101 in the contracted state in order for the delivery of the stent device 104 to occur through blood vessels of the patient and other narrow space. As shown in FIG. 2B, after the stent device 104, which is a self-expandable stent, reaches the treating portion and is pushed out from the stent delivery system 101, the stent body self-expands into the size for which it was designed for conducting treatment by expanding the treatment portion.

Figure 3:
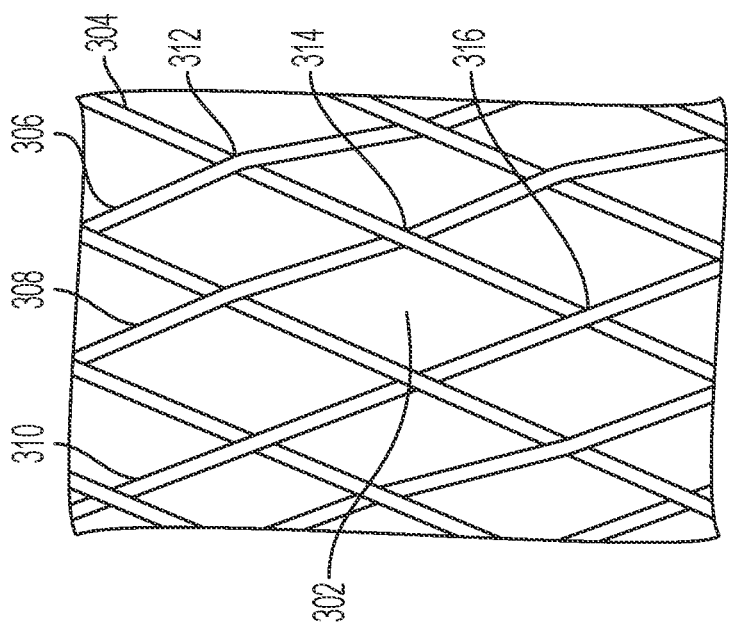

FIG. 3 illustrates a pattern of the stent wires comprising the stent body of the stent device 104. As disclosed in FIG. 3, the stent wires cross over each other and form cells enclosed by the stent wires, such as stent cell 302. The interconnection or overlap of the stent wires can be seen in FIG. 3 by, for example, observing the positional relationship of stent wire 304 as it intersects with stent wires 306, 308, and 310. The stent wire 304 intersects with stent wire 306 at intersection 312, where stent wire 304 goes under stent wire 306. The stent wire 304 then intersects with stent wire 308 at intersection 314, where stent wire 304 goes over stent wire 308. Then stent wire 304 goes under stent wire 310 at the next intersection 316. The alternating under and over location of wire 304 with respect to intersecting wires at each intersection repeats throughout the stent body shown in FIG. 3.

Figure 4:
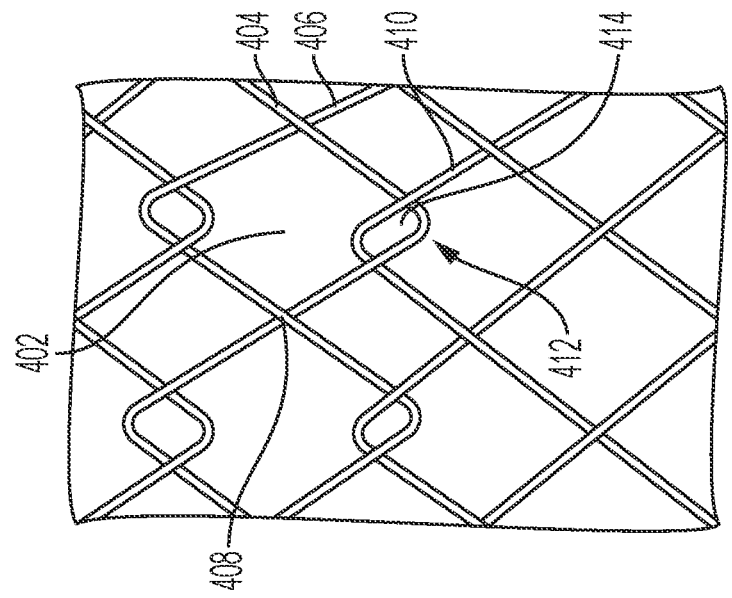
FIGS. 3 and 4 are magnified views of embodiments of a stent body and showing aspects of the stent wires.

FIG. 4 illustrates another pattern of the stent wires comprising the stent body of the stent device 104. As with FIG. 3, the stent wires of the stent device 104 cross over each other and form cells enclosed by the stent wires, such as stent cell 402. The interconnection or overlap of the stent wires in the stent body shown in FIG. 4 is more complex compared to that in FIG. 3. For example, the stent wires 404 and 406 cross over each other at intersection 408, but each of stent wires 404 and 406 bend and form an interlocking structure with a respective further stent wire, such as stent wires 404 and 410 forming an interlocking intersection 412. Because stent wires 404 and 410 can move independent of each other, stent wires 404 and 410 in the region of interlocking intersection 412 can form an interlocking stent cell 414.

Figure 5A:
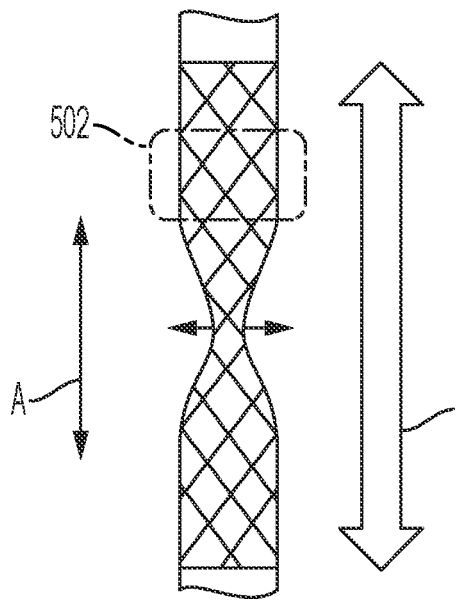
FIGS. 5A and 5B are schematic views of a stent device and, in magnified view in FIG. 5B, showing the arrangement of stent wires in a region of the stent body.
Figure 5B:
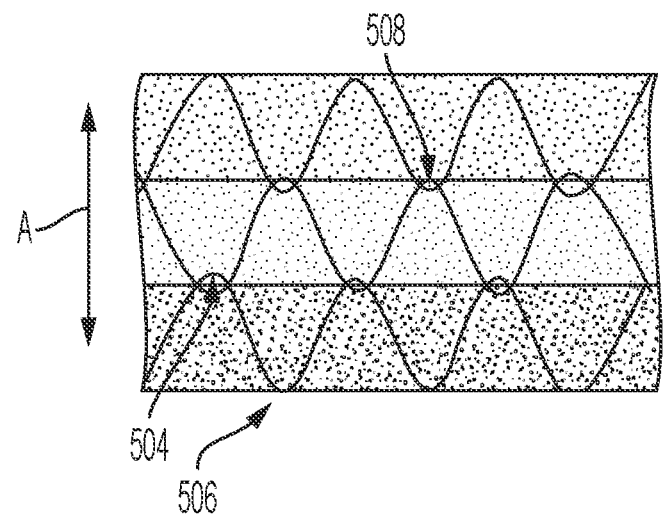
Figure 5C:
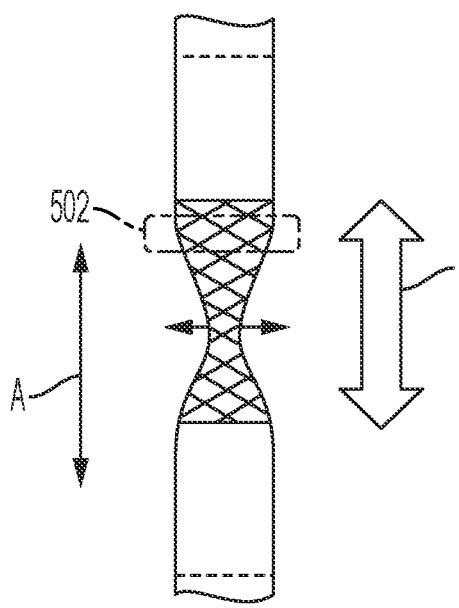
FIGS. 5C and 5D are schematic views of a stent device and, in magnified view in FIG. 5D, showing the arrangement of stent wires in a region of the stent body.
Figure 5D:
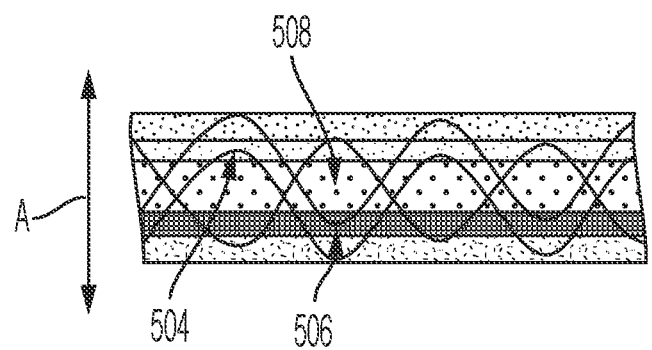

FIGS. 5A to 5D illustrate the mechanism of the axial shortening occurring in the stent device 104. FIG. 5B shows the magnified view of the area 502 in FIG. 5A and illustrates the stent wires of the stent body of a stent device 104 in which axial shortening has not occurred. In FIG. 5B, each stent wire is separated in the axial direction (represented by arrow A) with interlocking portions maximally separated in the axial direction with peaks 504 and valleys 506 of adjacent stent wires intersecting with each other. Depending on the similarity in structure of adjacent stent wires, the locations of intersection 508 can be evenly distributed. FIG. 5D shows the magnified view of the area 502 in FIG. 5C and illustrates an example of axial shortening. In FIG. 5D, stent wires are more closely packed with each other with peaks 504 and valleys 506 of adjacent stent wires no longer forming locations of intersection 508 and, because the stent wires have moved toward an overlapping arrangement, the stent wires are intermingled with each other. The axial shortening is apparent by comparing distance D1 in FIG. 5A with distance D2 in FIG. 5C.

Figure 6A:
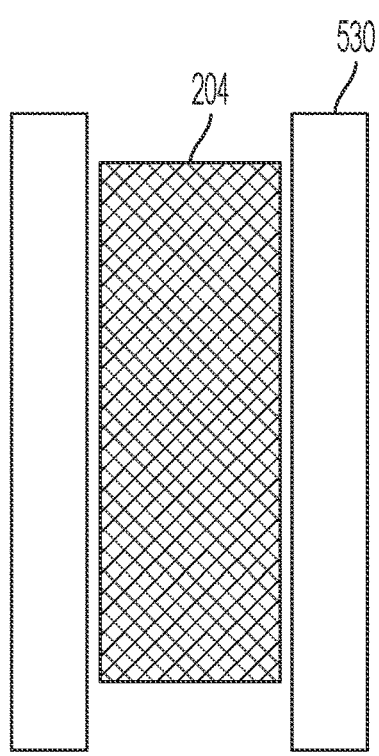
FIGS. 6A to 6C are schematic views of stent devices placed within a patient's body under straight and bent configurations.
Figure 6B:
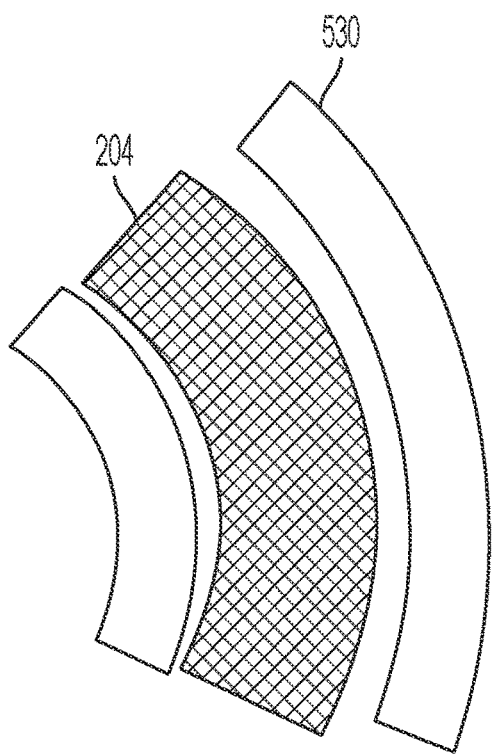
Figure 6C:
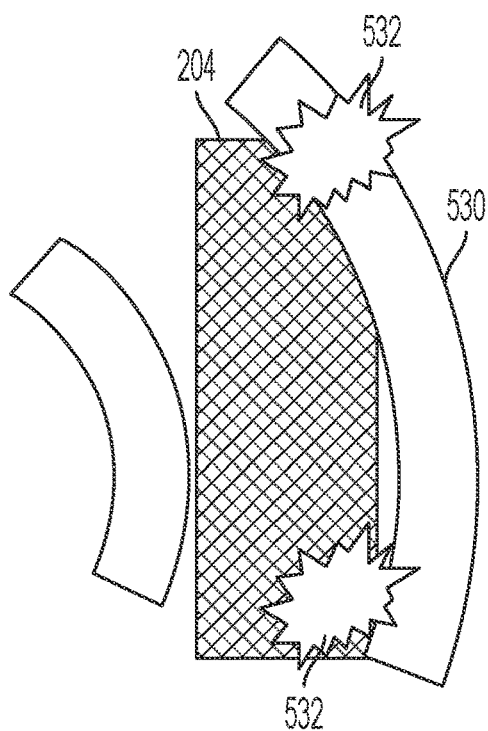

FIGS. 6A to 6C illustrate benefits of flexibility of the stent device after insertion into the patient's body. FIG. 6A discloses the stent device 104 inserted into a treatment portion 530 of a patient. In FIG. 6A, the stent device 104 is in a straight configuration. FIG. 6B discloses the stent device 104 inserted into a treatment portion 530 and in a bent configuration. Due to having adequate flexibility, the stent device 104 is able to bend in accordance with the bending angle of the treatment portion 530. However, as disclosed in FIG. 6C, the stent device 104 lacking adequate flexibility or even no flexibility would not be able to bend in accordance with the bending angle of the treatment portion 530. Due to this lack of flexibility, the stent device 104 would damage the treatment portion 530, such as by the edge or end of the stent device 104 extending into a portion of the treatment portion 530 of the patient's body (as shown at 532), either at time of insertion of the stent device 104 or anytime thereafter.

Figure 7A:
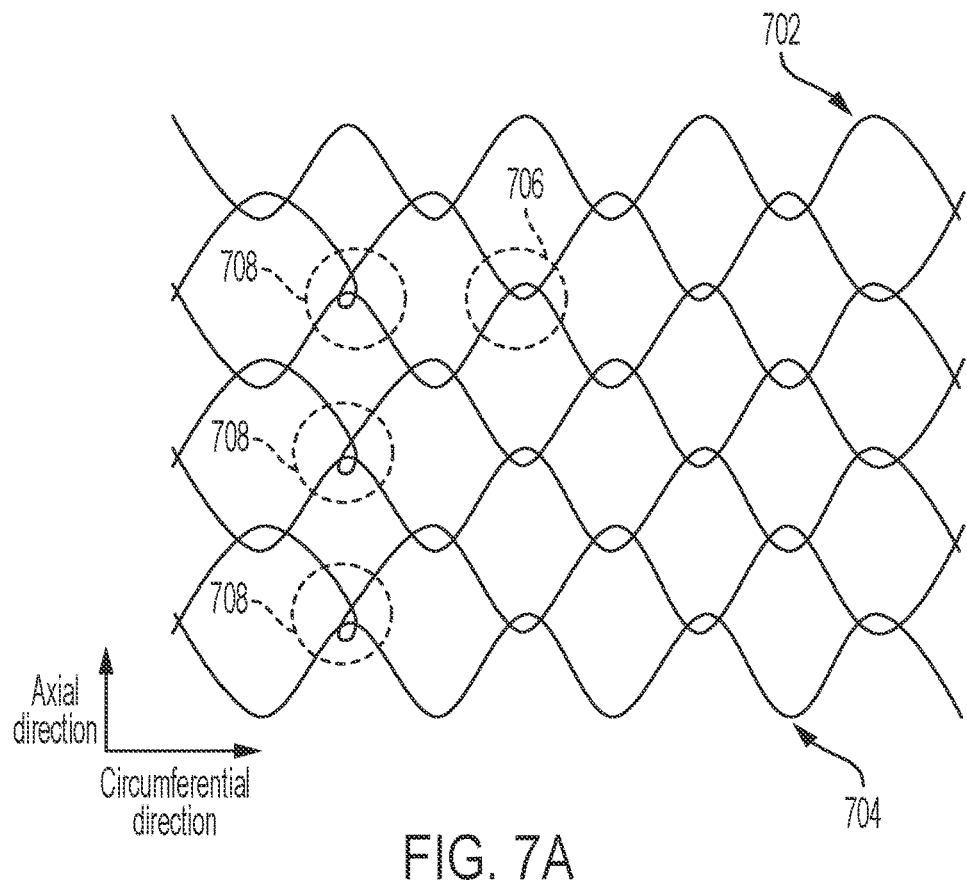
FIGS. 7A and 7B are schematic views showing aspects of stent wires having different interlocking features when the stent body is under different force conditions.
Figure 7B:
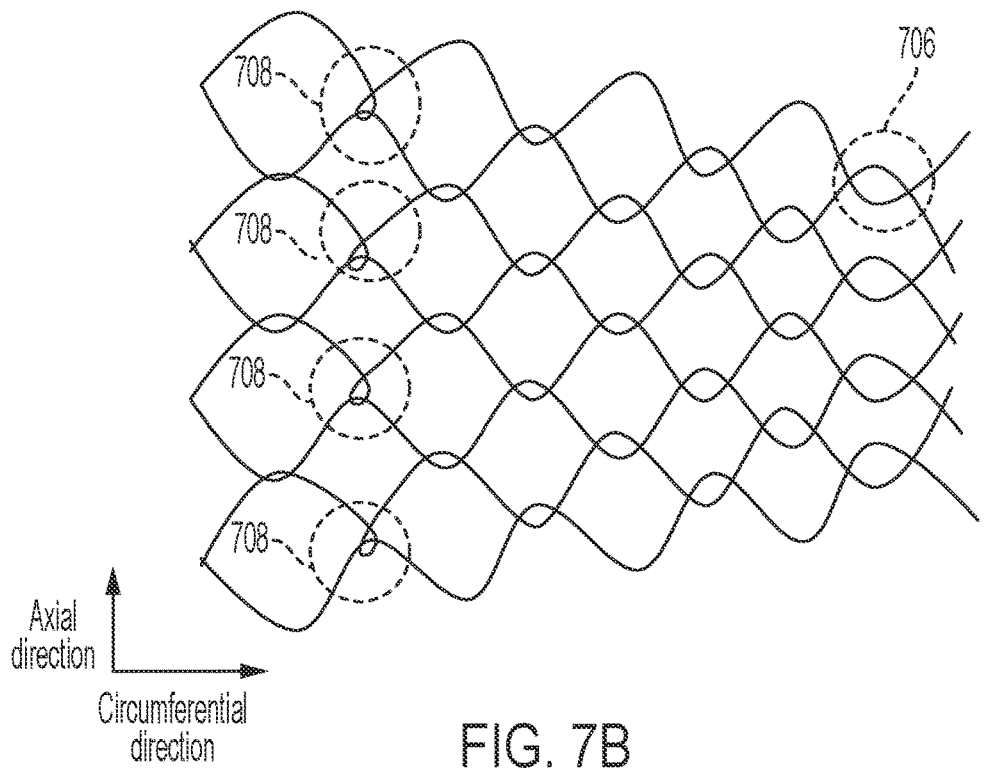

FIGS. 7A and 7B illustrates two types of interlocking structures of stent wires forming a stent body of a stent device. The stent wires are typically comprised of peaks and valleys (i.e. peak 702 and valley 704). The peaks and valleys in a given stent wire alternately repeats itself in the circumferential direction of the stent body. A first interlocking type 706 (also called a secondary interlocking structure) is shown in FIGS. 7A and 7B and is formed by two stent wires interlocking with each other by passing first stent wire over the second stent wire. In particular, the first interlocking type 706 is characterized by passing first stent wire over the second stent wire so that when the stent device is expanded in the axial direction, a peak 702 of a first stent wire is located at and passes over a valley 704 of second stent wire. Because of this arrangement of the first stent wire and second stent wire in first interlocking type 706, the peak 702 of one of the stent wires is located in the valley 704 of the other stent wire. A second interlocking type 708 (also called a primary interlocking structure) is also shown in FIGS. 7A and 7B and is formed by two stent wires interlocking with each other by a first stent wire forming a loop over a second stent wire (resulting in the second stent wire passing through the opening formed by the loop in the first stent wire).

As illustrated in FIG. 7B, the two stent wires forming the first interlocking type 706 can move relative to each other and loosen, which results in axial shortening in the case where a force is applied to the stent device in the axial direction. For example, the peak 702 of the first stent wire can move relative to the valley 704 of the other stent wire and the peak 702 become disengaged from the valley 704, e.g., the peak 702 of one of the stent wire can become unhung from the valley 704 of the other stent wire. In contrast and as also illustrated in FIG. 7B, the stent wires forming the second interlocking type 708 are constrained from moving relative to each other by the loop structure in that the stent wires forming the second interlocking type 708 do not become disengaged from each other, and the stent body having second interlocking type 708 structures do not exhibit axial shortening even in the case where a force is applied to the stent device in the axial direction. However, even though the stent wires forming the second interlocking type 708 do not become disengaged from each other, the first stent wire passing through the loop structure of the first stent wire can, in some embodiments, move such that the first stent wire moves in the circumferentially direction relative to the stent wire with the loop structure. Additionally, to the extent the first stent wire has a construction with some axial positional variation (such as a pattern of peaks and valleys), the two stent wires can, in some embodiments, also have relative motion in the axial direction, but such axial motion will be constrained by the distance from peak to valley on the respective first stent wire passing through the loop structure. Combinations of relative circumferential movement and relative axial movement may also occur in stent devices incorporating the second interlocking type 708.

Generally speaking, the stent device may be made by multiple stent wires or from a single stent wire. The interlocking structures may seem to require more than one stent wires to intertwine with each other, but a single stent wire may be used to circumvent the entire cylindrical stent structure through forming various interlocking structures by itself.

FIG. 8A is a chart disclosing the six exemplary types of interlocking portions that can be used to form the second interlocking type 708 structures of the stent body. The various exemplary types of second interlocking type 708 structures each includes at least one loop using the stent wires. In some embodiments, the second interlocking type 708 structure includes one loop on only first stent wire, and the other stent wire has no loop (i.e., is non-looped), in other embodiments, the second interlocking type 708 structure includes combinations of one or more loops on one of the two stent wires and none or one or more loops on the other of the two stent wires.

The following description of six exemplary types of interlocking portions is made with reference to FIGS. 8A to 8C. Second interlocking type no. ①  is formed by first stent wire forming a single loop and the other stent wire not forming a loop. Second interlocking type no. ①  is also shown in FIGS. 7A and 7B. Second interlocking type no. ② is formed by first stent wire forming a double-loop and the other stent wire not forming a loop. The stent wire without the loop can pass through the opening of either one or the other of the double-loop, although typically, the stent wire without the loop will pass through the distal of the two loops (as shown in FIG. 8A). FIG. 8B discloses the schematic view of Second interlocking type no. ②. A double-loop is formed between A and C, forming two intersections 802 and 804. Here, A to B is the "outward wire" and B to C is the "inward wire". In FIG. 8B, the outward wire passes under the inward wire at both intersection 802 and 804. Second interlocking type no. ③ is similar to Second interlocking type no. ②. FIG. 8C discloses the schematic view of Second interlocking type no. ③. A double-loop is formed between A and C, forming two intersections 806 and 808. Here, A to B is the "outward wire" and B to C is the "inward wire". In FIG. 8C, the outward wire passes under the inward wire at intersection 802 and outward wire passes over the inward wire at 804. In other words, in Second interlocking type no. ③, the stent wire that is on the top at intersection 806 is different from the stent wire that is on top at intersection point 808. Thus, unlike Second interlocking type no. ②, the outward and inward wires are twisted in Second interlocking type no. ③, making the double-loop for Second interlocking type no. ③ tighter than Second interlocking type no. ②. The stent wire without the loop can pass through the opening of either one or the other of the double-loop, although typically, the stent wire without the loop will pass through the distal of the two loops (as shown in FIG. 8A). Second interlocking type no. ④ is formed by both stent wires forming a single loop. The two single loops are interconnected with each other as shown in FIG. 8A. Second interlocking type no. ⑤ is formed by first stent wire forming a double-loop and the other stent wire forming a single loop. The single loop is interconnected with double-loop by the wire of the single loop passing through one of the openings of either one or the other of the double-loop, although typically, the single loop will pass through the distal of the two loops (as shown in FIG. 8A). Finally, second interlocking type no. ⑥ is formed by both stent wires forming a double-loop. The loop of first stent wire is interconnected with a loop of the second stent wire, although typically, the distal loops of both double-loop structures will pass through each other (as shown in FIG. 8A). As disclosed in FIG. 8C, the intertwining of the outward and inward wires may be made more complex structure (i.e. twisted) in order to make the double-loop structure for Second interlocking type no. ⑤ and ⑥ tighter as compared to the structure disclosed in FIG. 8B.

Figures 8D, 9:
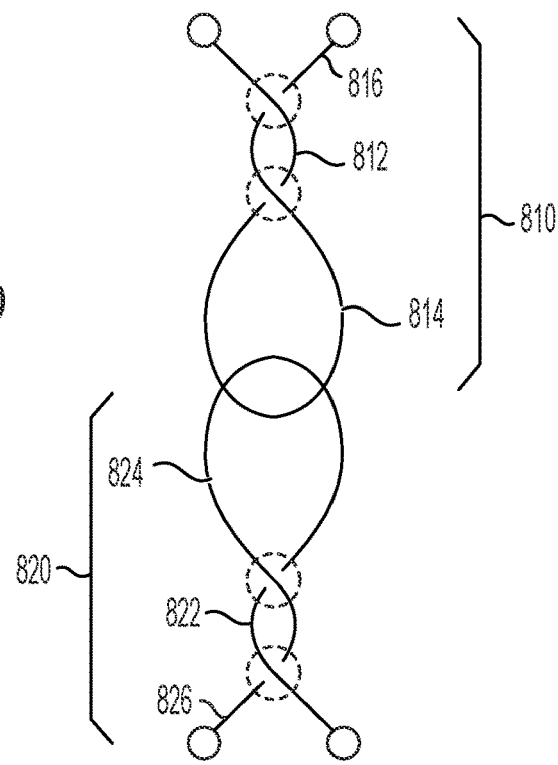

FIG. 8D shows an embodiment with two double-loop structures, including a first double-loop structure 810 with a first loop 812 and a second loop 814 on a first stent wire 816 and a second double-loop structure 820 with a third loop 822 and a fourth loop 824 on a second stent wire 826.

Depending on the combination of non-loop, single loop, and double-loop on the two stent wires, the axial shortening and flexibility (bending) can vary. For example, and as shown in FIG. 8A, the level of axial shortening increases from second interlocking type no. ① to no. ⑥ and the level of flexibility of the stent device increases from second interlocking type no. ⑥ to no. ①, due to the number of loops involved.

FIG. 9 is a chart disclosing the four factors (factors Ⓐ to Ⓓ) that may affect the functions of each loops included in the various second interlocking types. Factor Ⓐ is the size of the loop. Increasing the size of the loop increases the degree of freedom of the stent wires at the interlocking portions and improves the overall flexibility of the stent device. Factor Ⓑ is the shape of the loop. The asymmetrical shape of the loop may create unevenness in the flexibility of the stent wires forming the loop, resulting in unevenness in the flexibility of the interlocking portion. Factor Ⓒ is direction of the loop rotation. By changing the direction of the rotation of the loop, it is possible to adjust the direction of the increased flexibility and decreased flexibility of the stent wires constituting the interlocking portion. Factor Ⓓ is the rise of the loop. The raised structure of the loop makes the surface of the stent device uneven, which may minimize or prevent migration of the stent device within the treatment portion of the patient.

Figure 10A:
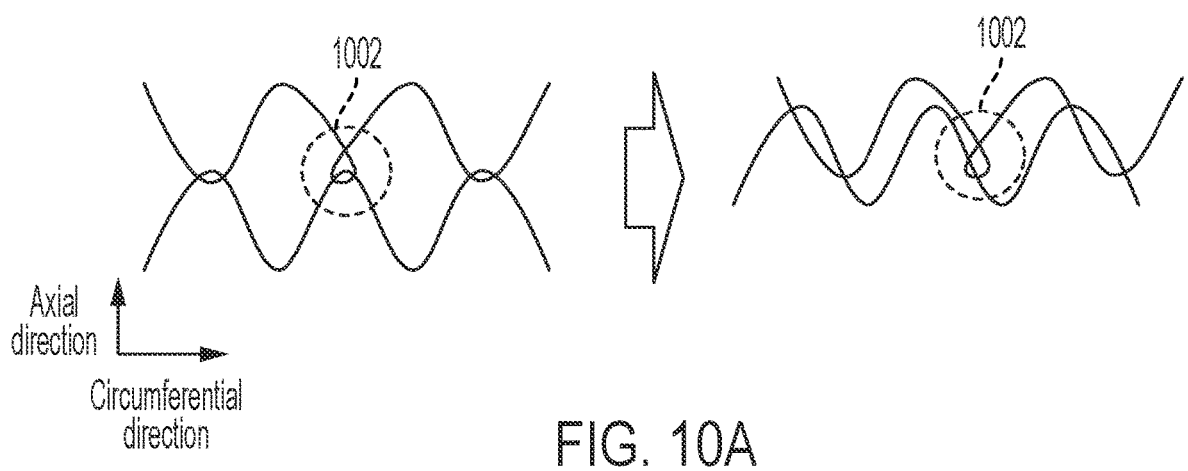
FIGS. 10A and 10B are schematic views showing embodiments of the structures of the interlocking portions of the stent wire.
Figure 10B:
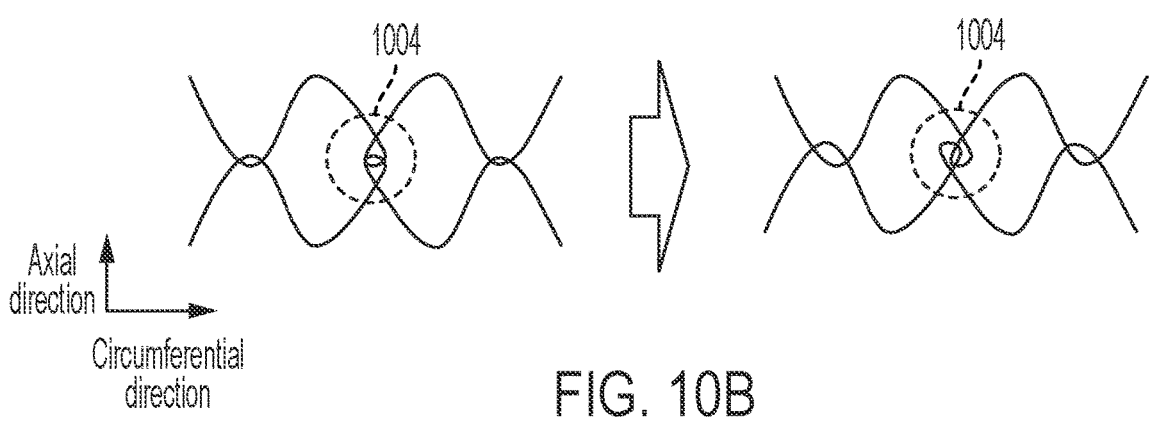

FIGS. 10A and 10B illustrate how forming loops in both stent wires (i.e. second interlocking type nos. ④, ⑤, and ⑥) prevents axial shortening of the stent device. FIG. 10A shows two stent wires forming a single Second interlocking portion type no. ①. In case a force is applied to the stent device in the axial direction, the loop 1002 in the Second interlocking portion type no. ① slides along the other stent wire, e.g., movement in the circumferential direction, reducing the distance (in the axial direction) between stent wires and allowing axial shortening of the stent device to occur. In contrast, as shown in FIG. 10B, the two stent wires forming a single Second interlocking portion type no. ④ with one loop formed on each of the stent wires, the loops 1004 formed on both stent wires prevent the sliding of the loops 1004 and contribute to maintaining the distance (in the axial direction) between stent wires and prevent axial shortening of the stent device from occurring. Second interlocking portion ⑤ and ⑥, in which both first wire and the second wire form a loop, have the same effect as Second interlocking portion type no. ④.

Figure 11A:
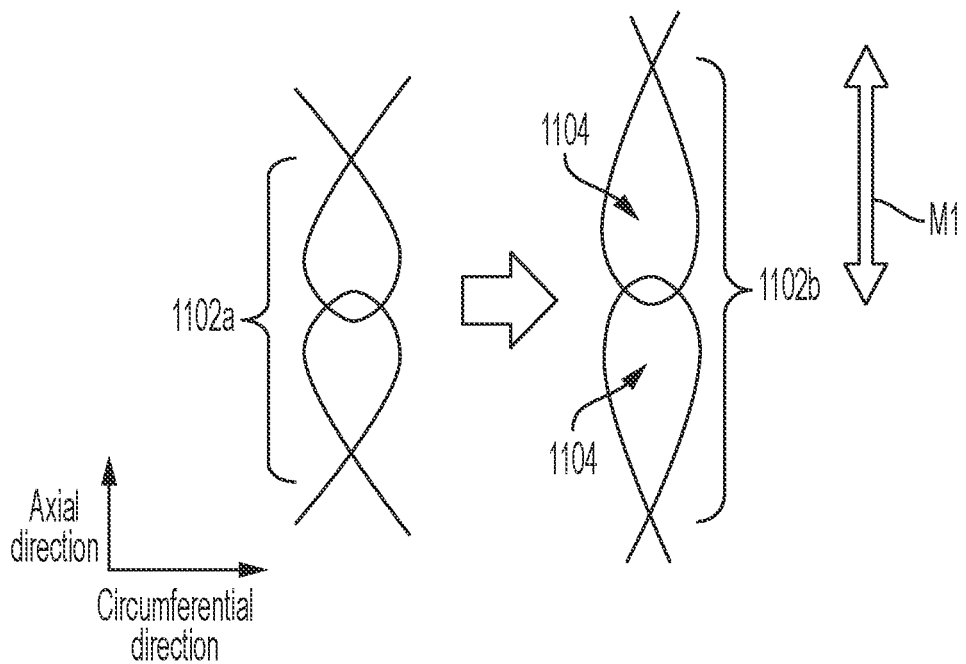
FIGS. 11A and 11B are schematic views showing embodiments of the structures of the interlocking portions of the stent wire.
Figure 11B:
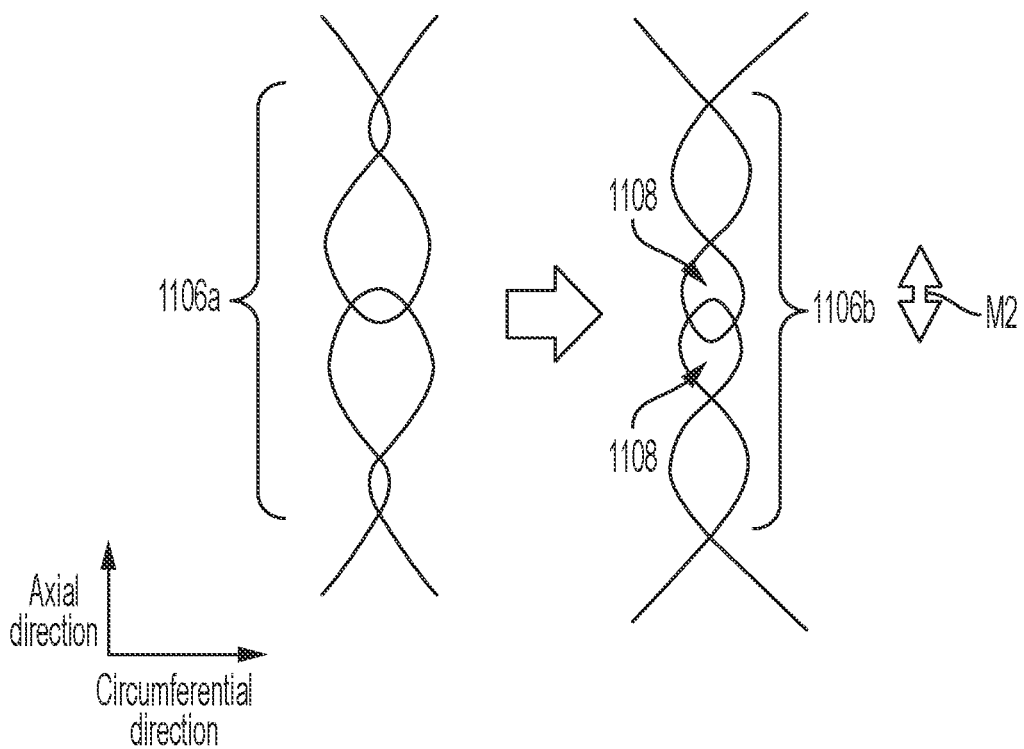

FIGS. 11A and 11B illustrates how forming double-loops in both stent wires (i.e. Second interlocking portion type no. ⑥) prevents axial shortening of the stent device. FIG. 11A discloses two stent wires forming Second interlocking portion type no. ④ with one loop formed on each of the stent wires. Through contraction of the stent device, such as is necessary for embedding the stent delivery system as described in FIG. 2A, a force in the circumferential direction is applied to the stent wires. As disclosed in FIG. 11A, after the force applied in the circumferential direction, the shape of the loop is extended in the axial direction (compare distance 1102a to distance 1102b), which can provide more space for axial shortening to occur in case a force is applied in the axial direction. For example, the open space 1104 within each loop provides freedom of movement in the axial direction to the stent wires, which can move as indicated by arrow M1. In contrast, as shown in FIG. 11B, when the two stent wires form Second interlocking portion type no. ⑥ with double-loops formed on both stent wires, the difference in axial distance between the shape of the loops when a force is applied in the circumferential direction (right side of FIG. 11B) and when a force is not applied in the circumferential direction (left side of FIG. 11B) (compare distance 1106a to distance 1106b) is much less than in the FIG. 11A configuration. Also, although the overall length in the axial direction is related to the axial length of the double-loop structure, the open space 1108 in the loops that are interconnected provides space for freedom of movement in the axial direction for the stent wires which is limited as indicated by arrow M2. As the distance M2 is less than the distance M1, the double-loops in FIG. 11B minimizes and prevents axial shortening in the case a force is applied in the axial direction upon or after the stent device is put in a contracting state to a greater extent than the single loop structure in FIG. 11A.

Figure 12:
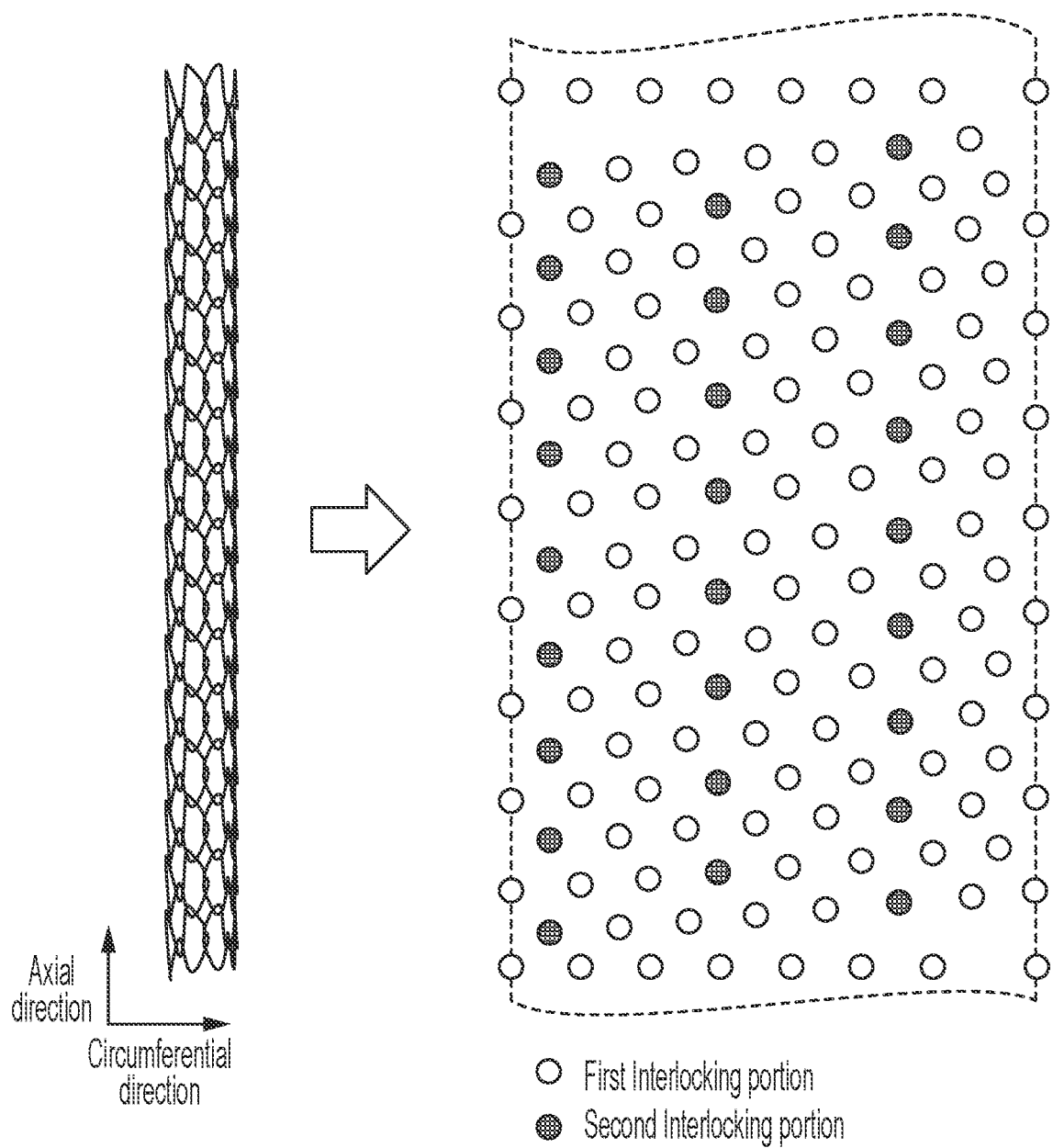
FIG. 12 is a schematic view showing the location, distribution, and positional relationship of the interlocking portions in a stent device.

FIG. 12 illustrates the allocation of the two variations of interlocking portions, the First Interlocking portion and Second Interlocking portion within the stent device. The First Interlocking portion has connections between the stent wires consistent with first interlocking portion types disclosed herein and the Second Interlocking portion has connections between the stent wires consistent with Second interlocking portion types disclosed herein. The schematic on the right shows the location of the two different interlocking portions of the cylindrical stent device, where the cylindrical stent device has been illustrated as a sheet-like structure. The open dot represents the First Interlocking portion, e.g., the structure having no loop within the interlock structure, and the filled dot represents the Second Interlocking portion, e.g., the structure having at least one loop within the interlock structure. In the FIG. 12 embodiment, the Second Interlocking portions are linearly located in the axial direction.

Figure 13:
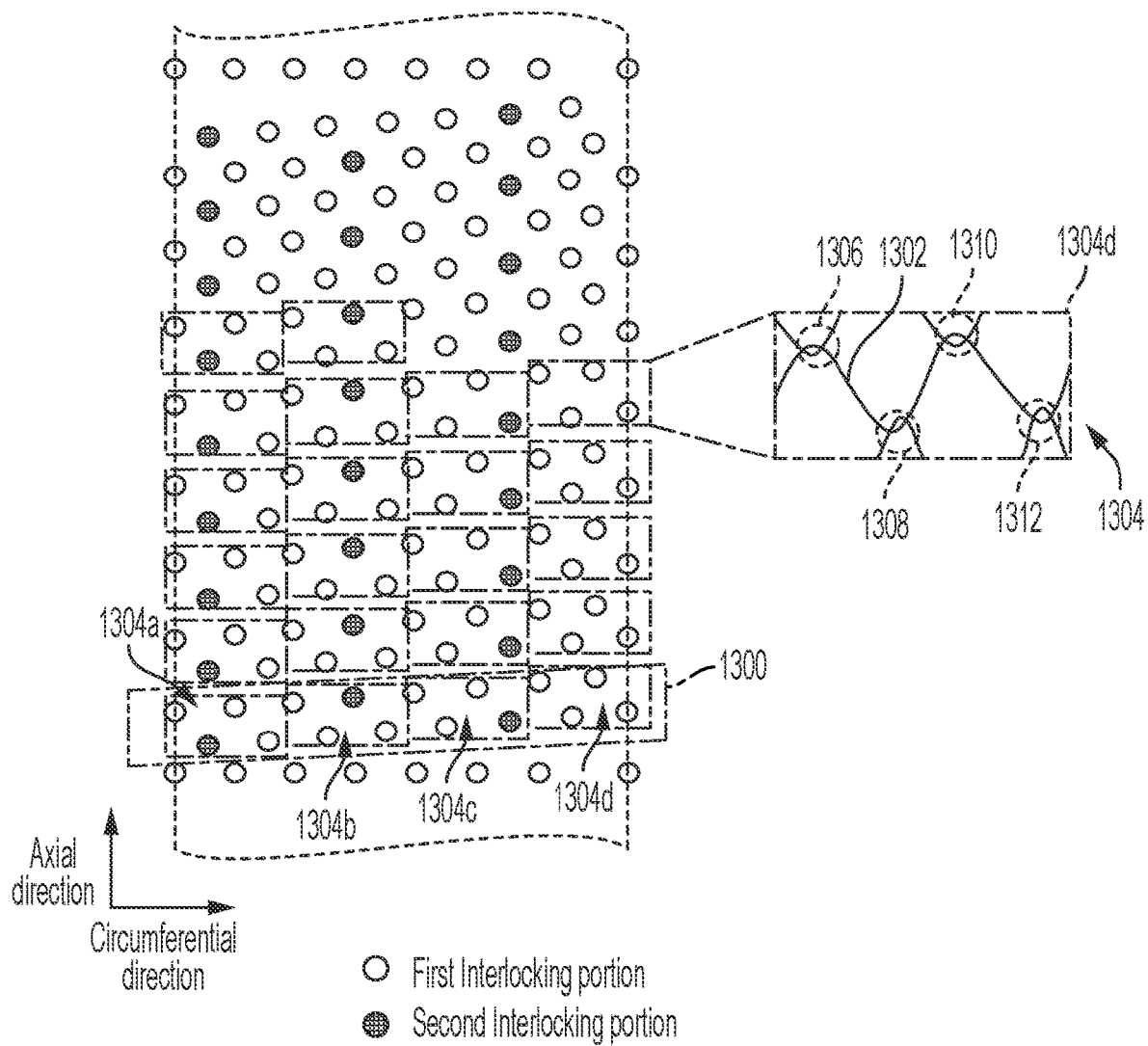
FIG. 13 is a schematic view showing the allocation of the interlocking portions in a stent device and showing details and arrangement of interlocking blocks in one embodiment.

FIG. 13 illustrates the relationship of the four neighboring interlocking portions (in the circumferential direction) sharing a single stent wire 1302, forming interlocking block 1304. As disclosed in FIG. 13, interlocking block requires a stent wire to interlock with the two adjacent stent wires forming four consecutive interlocking portions. There is a plurality of such interlocking blocks 1304 that extend across the length of the stent device in the circumferential direction (for example, the four interlocking blocks 1304 in area 1300 shown in FIG. 13 forming a row of interlocking blocks 1304). A plurality of such rows of interlocking blocks 1304 extend in the axial direction. Within each row of interlocking blocks 1304, the arrangement of the four neighboring interlocking portions contained within one interlocking block 1304 varies. For example, each of interlocking block 1304a, 1304b, 1304c in area 1300 has one Second Interlocking portion and three First Interlocking portion (as indicated by the open dot (representing First Interlocking portion) and the filled dot (representing Second Interlocking portion)) and interlocking block 1304d within area 1300 has no Second Interlocking portion. A magnified view of interlocking block 1304*d* is shown in FIG. 13. In the magnified view of interlocking block 1304*d*, the single stent wire 1302 interlocks with the other two stent wires at interlocking portions 1306, 1308, 1310, and 1312, each of the four interlocking portions being a First Interlocking portion.

As shown in FIG. 13, the location of the Second Interlocking portion among the four neighboring interlocking portions in any one interlocking block 1304 changes within the stent device as a function of location in the circumferential direction. Thus, in interlocking block 1304*a*, the Second Interlocking portion is the second location; in interlocking block 1304*b*, the Second Interlocking portion is the third location; and in interlocking block 1304*c*, the Second Interlocking portion is the fourth location.

Figure 14A:
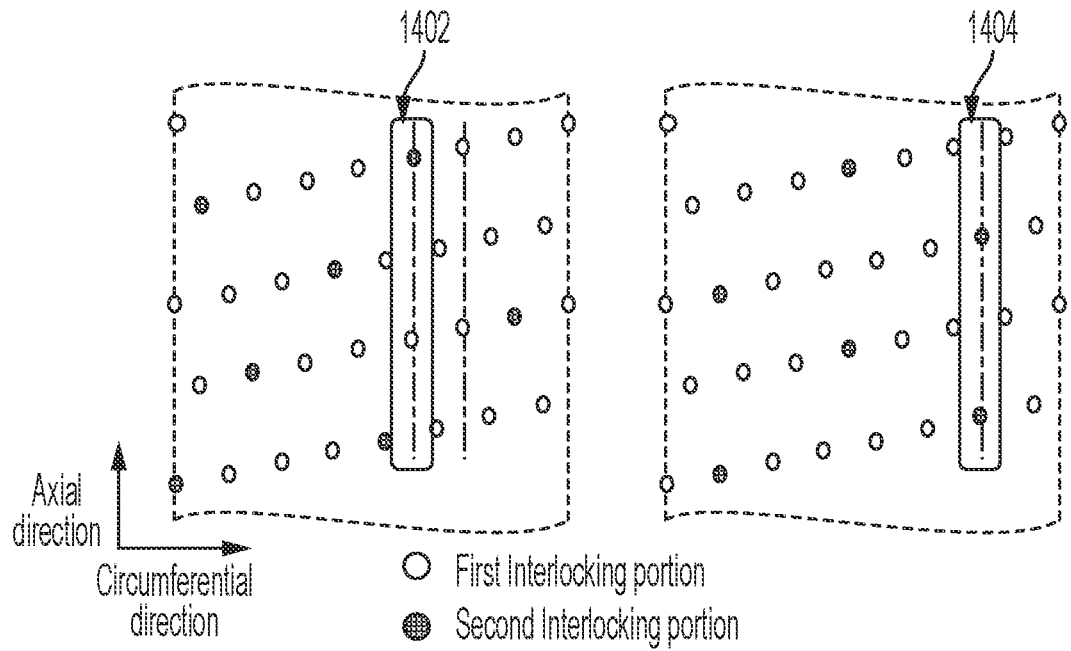
FIGS. 14A and 14B are schematic views showing the allocation of the interlocking portions in a stent device and showing details and arrangement of interlocking blocks in other embodiments.

FIG. 14A is a schematic representation of a stent body showing alternate allocations (numbers and locations) of First Interlocking portions and Second Interlocking portions. Interlocking block 1402 discloses two interlocking portions aligned in the axial direction where one of the interlocking portions is a First Interlocking portion and the other is a Second Interlocking portion. Interlocking block 1404 discloses two interlocking portions aligned in the axial direction where both of the interlocking portion is the Second Interlocking portion. Interlocking block 1404, two or more of the Second Interlocking portions are placed in the same line in the axial direction. This configuration can prevent axial shortening of the stent device better than Interlocking block 1402. The Second Interlocking portions do not necessarily need to align in a continuous manner. A plurality of the Second Interlocking portions arranged in the same axial direction contributes to preventing axial shortening of the stent device.

Figure 14B:
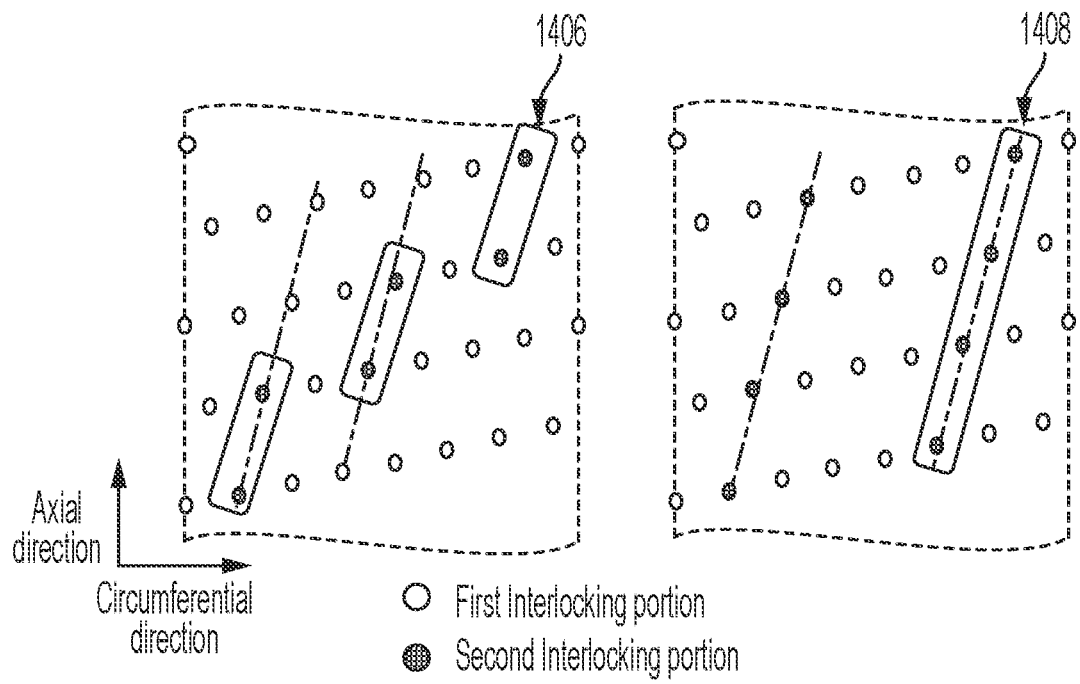
Figure 15A:
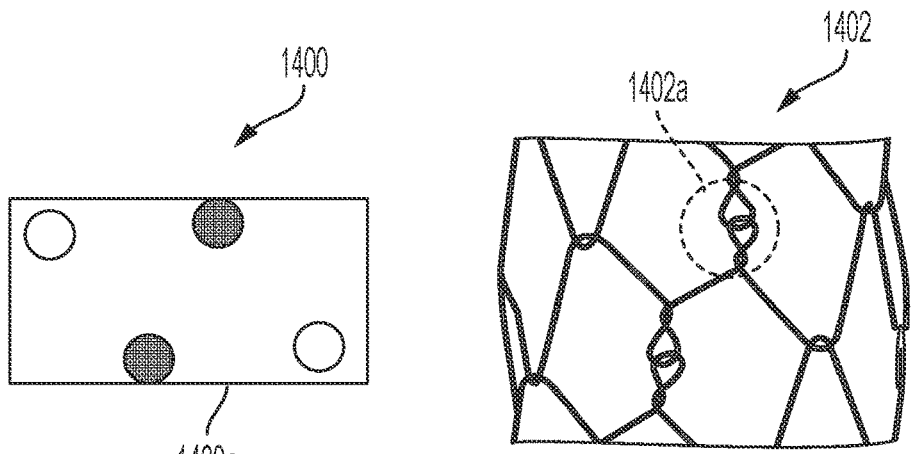
FIGS. 15A to 15D are schematic views of the interlocking portions and comparison picture of an example stent device.
Figure 15B:
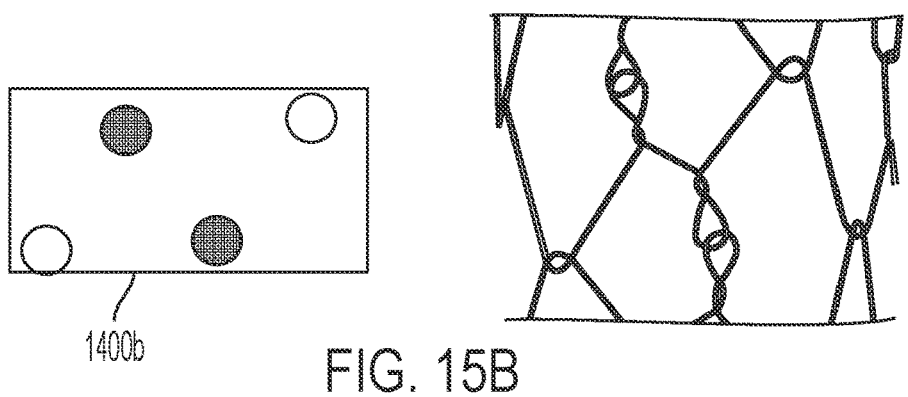
Figure 15C:
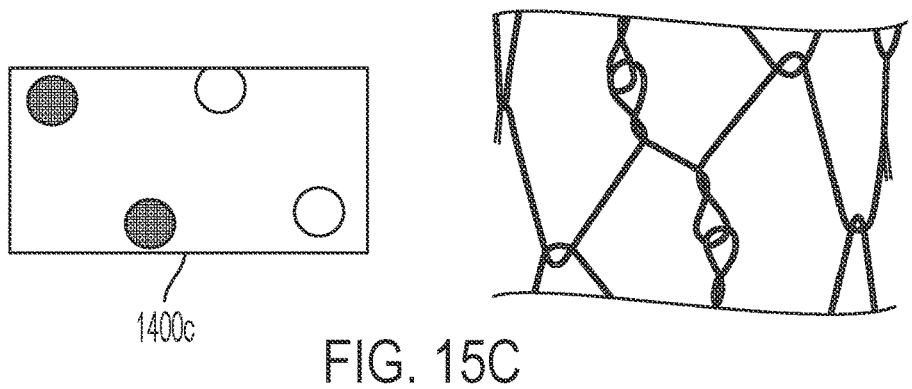
Figure 15D:
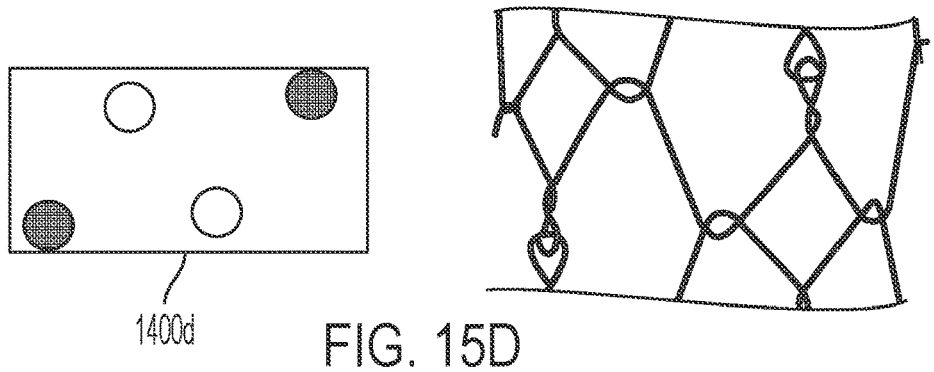

FIG. 14B is another schematic representation of a stent body showing alternate allocations (numbers and locations) of First Interlocking portions and Second Interlocking portions. Interlocking block 1406 discloses two consecutive Second Interlocking portions aligned in the inclined direction. In other words, in Interlocking block 1406, Second Interlocking portions are formed on the continuous peak and valley of the stent wire. This prevents axial shortening of the stent device more than Interlocking block 1402. Interlocking block 1408 discloses four consecutive Second Interlocking portions aligned in the inclined. This configuration in Interlocking block 1408 can prevent axial shortening of the stent device better than Interlocking block 1406. Placing more Second Interlocking portions in the inclined direction than Interlocking block 1406 will contribute to preventing axial shortening of the stent device, but the number of Second Interlocking portions need not be four.

FIGS. 15A to 15D illustrates various interlocking blocks 1400 relative to the actual implementation 1402 in the stent device. FIGS. 15A to 15D disclose interlocking blocks 1400*a*, 1400*b*, 1400*c*, 1400*d*, each of which include two First Interlocking portions (i.e. including no loop) (indicated by open dot) and two Second Interlocking portions (i.e. including at least one loop) (indicated by filled dot). FIGS. 15A to 15D disclose Second Interlocking portion 1402*a* in the form of second interlocking type no. ⑥, in which both stent wires comprising the interlocking portions include double-loops.

Figure 16A:
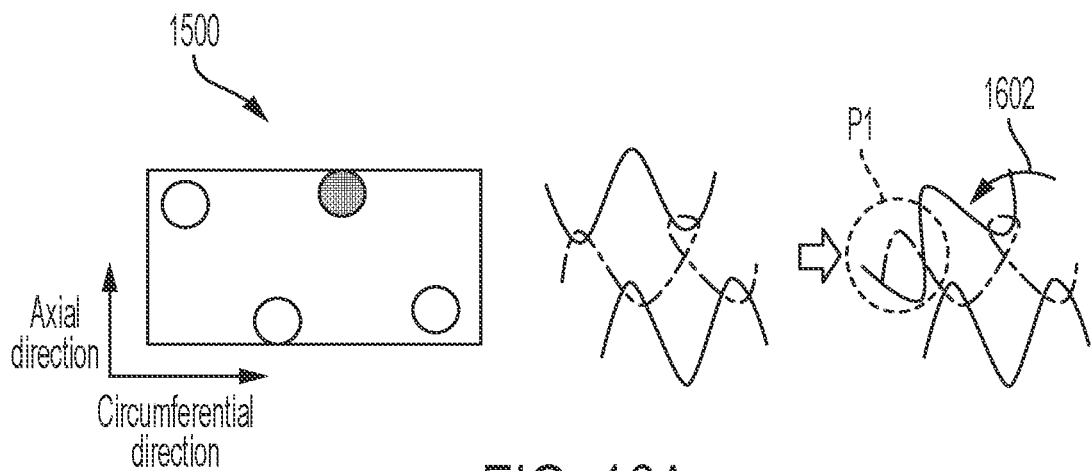
FIGS. 16A to 16C are schematic views of the interlocking portions showing the effects of different interlocking portions to the flexibility of the stent device.
Figure 16B:
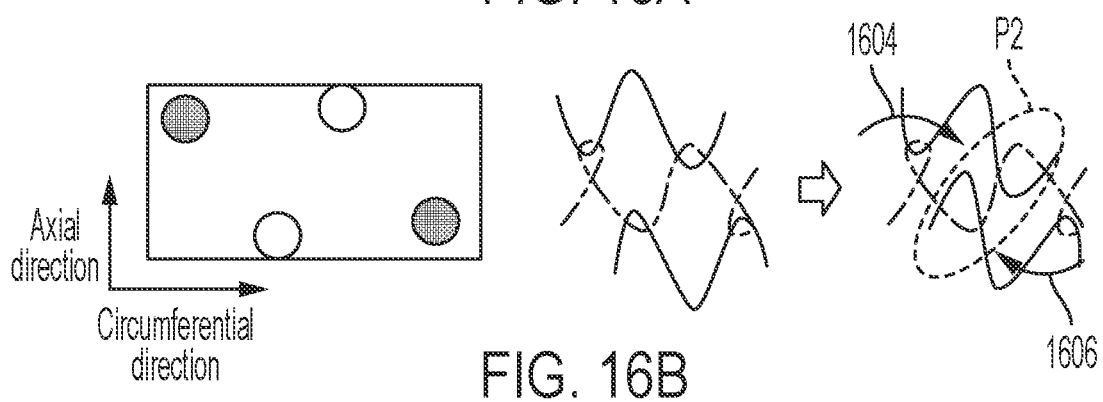
Figure 16C:
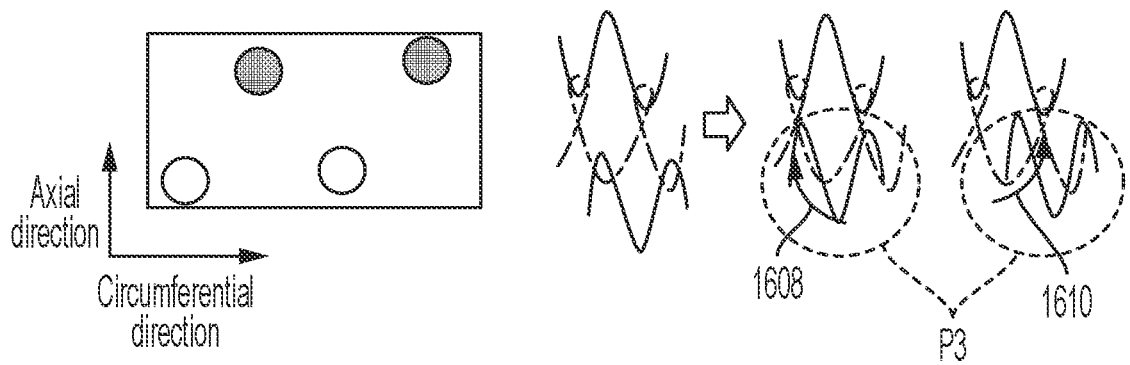

FIGS. 16A to 16C illustrates the relationship between the allocation, e.g., number and location, of the Second Interlocking portions within an interlocking block 1500 and the effects of such different allocations on the flexibility of the stent device. FIG. 16A discloses an interlocking block with one Second Interlocking portion (second interlocking type no. ①) (represented by filled dots) and three First Interlocking portions (first interlocking type, i.e. with no loop) (represented by open dots). The line schematics illustrate the relationships of the stent wires and how the Second Interlocking portion interacts with the First Interlocking portions. The line schematics show that when a force is applied to the stent device in the circumferential direction (arrow 1602), the loosely interlocked First Interlocking portions provide leeway to the stent wires to intermingle, resulting in flexibility of the stent device (see e.g., region P1 where the stent wires in the First Interlocking portion have moved apart and separated). However, Second Interlocking portions maintain their interlocking relationship.

FIGS. 16B and 16C discloses other examples of interlocking blocks with two Second Interlocking portions (second interlocking type no. ①) (represented by filled dots) and two First Interlocking portions (first interlocking type, i.e. with no loop) (represented by open dots). The line schematics also show that when a force is applied to the stent device in the circumferential direction (arrows 1604, 1606, 1608, and 1610), the loosely interlocked First Interlocking portions provide leeway to the stent wires to intermingle, resulting in flexibility of the stent device (see e.g., regions P2 and P3, where the stent wires in the First Interlocking portions have moved apart and separated). However, Second Interlocking portions maintain their interlocking relationship.

The ratio of a number of the Second Interlocking portions against the First Interlocking portions is ideally 1:3 or 2:2, or alternatively 0.15 to 0.60, 0.15 to 0.40, 0.15 to 0.30, 0.25 to 0.40, or 0.40 to 0.60.

Figure 17:
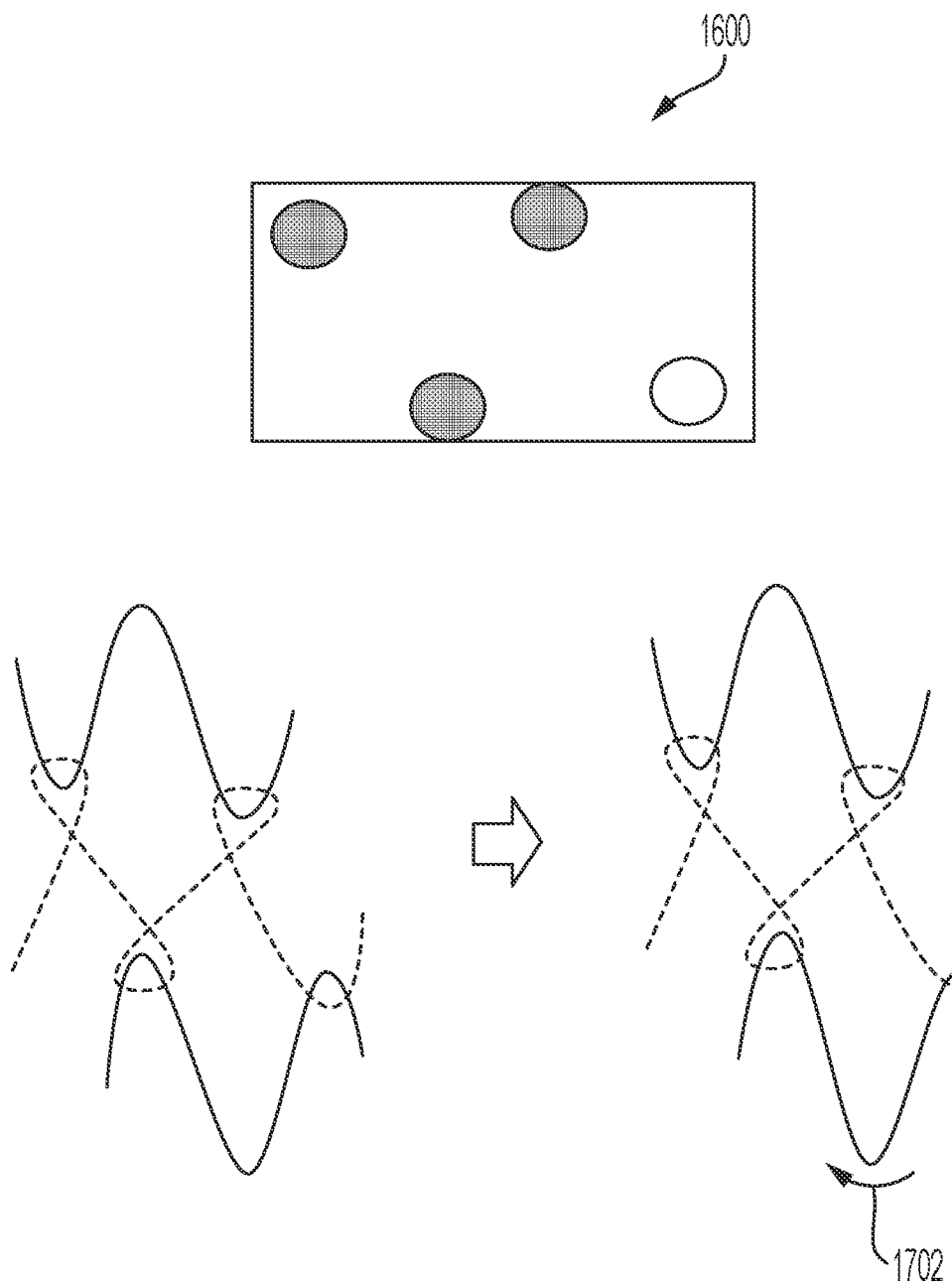
FIG. 17 is a schematic view of the interlocking portions showing the effects to the flexibility of the stent device for another interlocking portion.

FIG. 17 illustrates an interlocking block 1600 with three Second Interlocking portions (second interlocking type no. ①) (represented by filled dots) and one First Interlocking portion (first interlocking type, i.e. with no loop) (represented by open dots). The line schematics show that, in this embodiment, when a force is applied to the stent device in the circumferential direction (arrow 1702), the loosely interlocked First Interlocking portion does not provide leeway to the stent wires to intermingle, resulting in no flexibility of the stent device. This lack of flexibility is generally seen in interlocking blocks including three or more Second Interlocking portions.

Figure 18:
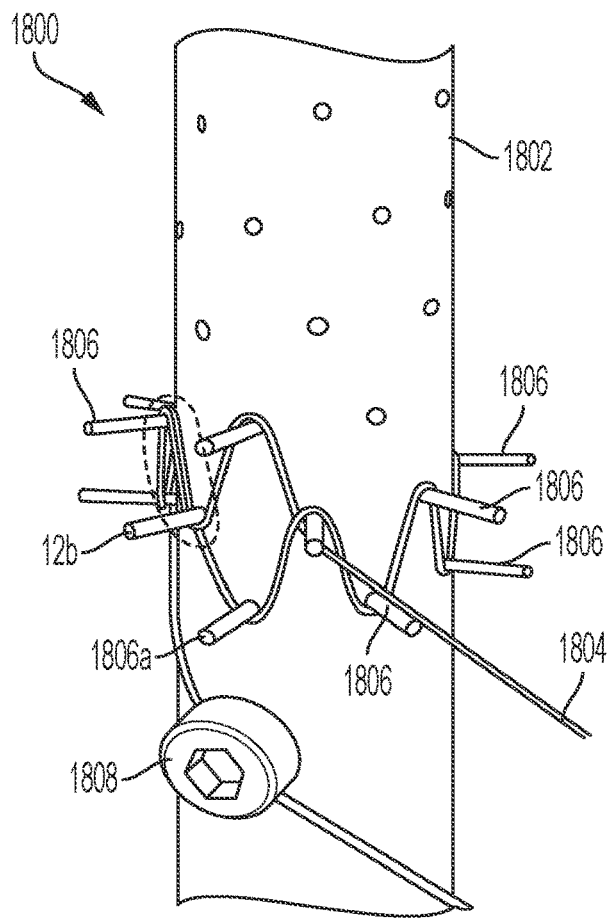
FIGS. 18 and 19 illustrates examples of a method for manufacturing of the stent device.

FIG. 18 illustrates an example of a method for manufacturing of the stent device. The method of manufacturing a stent device includes a process of preparing a jig 1800 having a cylindrical shaft 1802, and a braiding process of winding at least one stent wire 1804 from a proximal end of the shaft 1802 to a distal end of the shaft 1802 in a spiral around a longitudinal axis of the shaft 1802. The jig 1800 has a plurality of pins 1806 that are attached to the outer periphery of the shaft 1802, and holes are formed at transition points on the outer periphery of the shaft 1802 for inserting the pins 1806. The holes in the shaft 1802 correspond to the open dots of the First Interlocking portion and filled dots of Second Interlocking portion illustrated in FIG. 12. The holes in the shaft 1802 are located at the intersection of a plurality of circumferential dividing lines that extend in the longitudinal direction of the shaft 1802 and equally divide the circumference of the shaft 1802 into a plurality of pieces, and a plurality of length dividing lines that extend in the circumferential direction of the shaft 1802 and equally divide the length of the shaft 1802 into a plurality of portions. In the process of preparing the jig 1800, a pin 1806 is attached to each hole of the shaft 1802. The multiple pins 1806 attached to the holes are arranged along a spiral path around the longitudinal axis of the shaft 1802.

During the braiding process, one end of the stent wire 1804 is secured to an anchor pin 1808, and the stent wire 1804 is extended from the anchor pin 1808 to the starting pin 1806*a*, which is the nearest pin located on the length division line. The stent wire 1804 is extended in the circumferential direction of the shaft 1802 from the starting pin 1806*a* and wound in a zigzag manner around the longitudinal axis of the shaft 1802. This forms a plurality of wound stent wires 1804. At this time, the stent wire 1804 is extended in a zigzag manner in the circumferential direction while alternately passing through pins 1806 on one length division line and pins 1806 on other length division lines adjacent to the distal side of one length division line. This forms the peak on the pin 1806 on one length division line and the valley on the pin 1806 on the other length division line.

Figure 19:
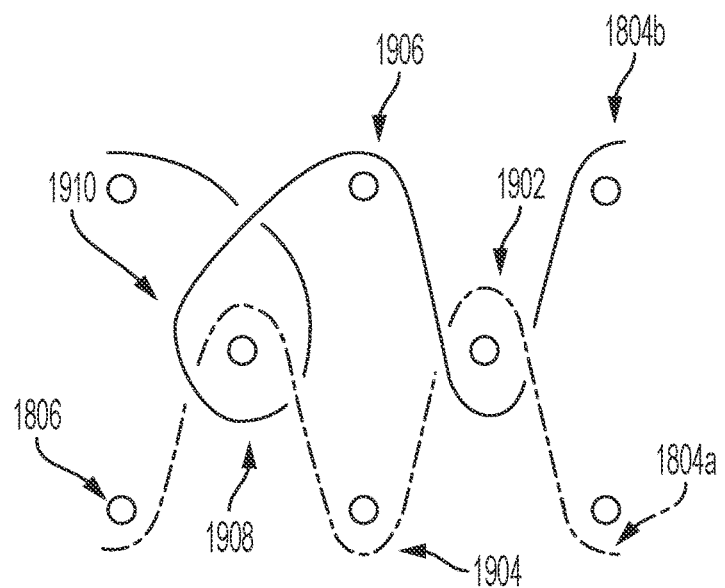
Figure 20:
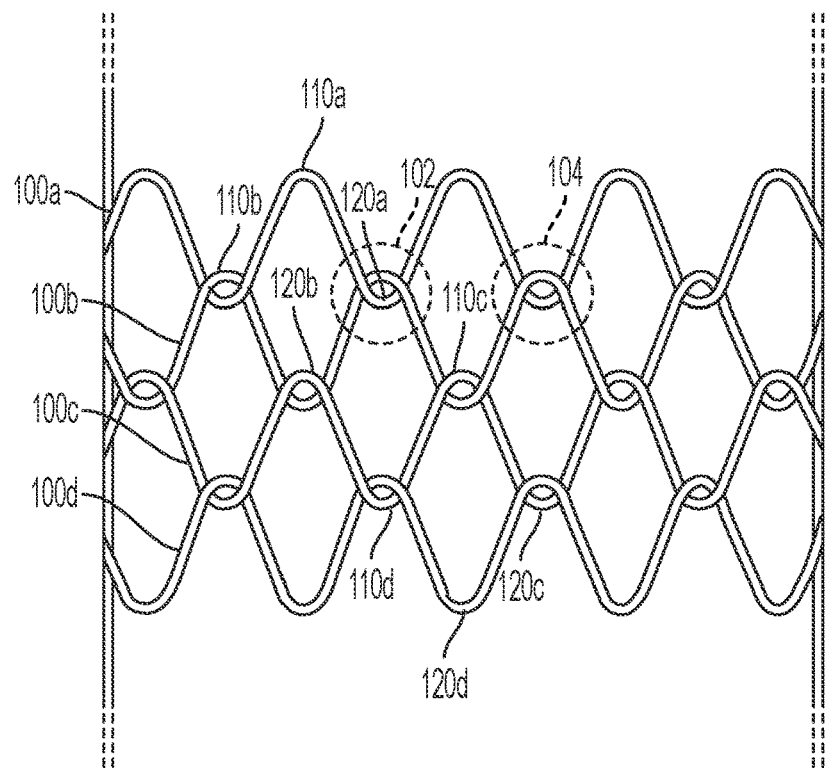
FIGS. 20 and 21 show related art stent devices.
Figure 21:
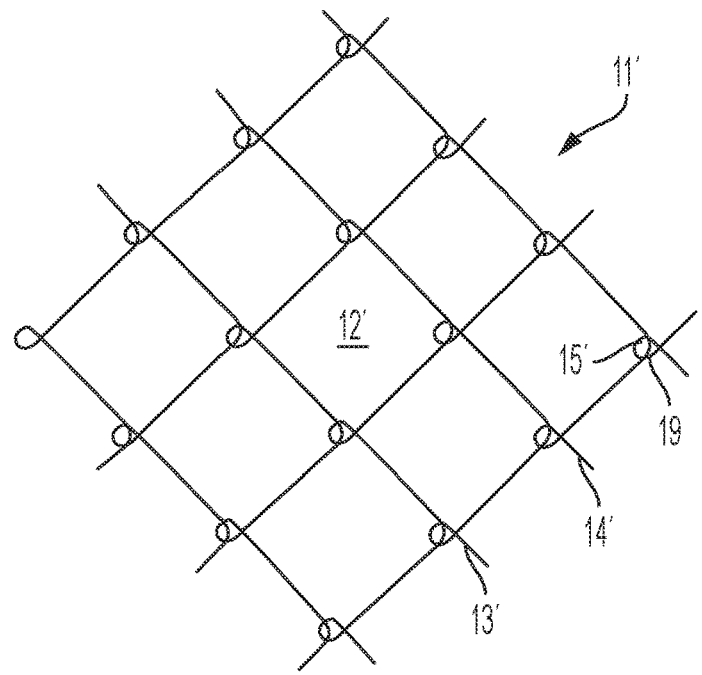

FIG. 19 further illustrates an example of a method for manufacturing of the stent device. As described in FIG. 18 stent wires 1804*a* extends in the circumferential direction while alternately passing through pins 1806 in a zigzag manner forming peak 1902 and valley 1904. The stent wire 1804*b* also extends in the circumferential direction while alternately passing through pins 1806 in a zigzag manner forming peak 1906 and valley 1908. The stent wire 1804*b* may form a loop around the pins 1806 and interlock with the stent wire 1804*a*, forming a loop 1910 at the second valley 1908 of the stent wire 1804*b*, which may be a single loop or multiple loops, forming the various types of interlocking portions described in the aforementioned embodiments.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A stent device, comprising:
   a first stent wire and a second stent wire forming a cylindrical stent body, wherein the cylindrical stent body encloses an interior void space and defines an inner luminal side of the stent body;
   a primary interlocking structure; and
   a secondary interlocking structure,
   wherein the primary interlocking structure includes (i) a first double-loop structure including a first loop formed of the first stent wire and defining a first loop opening and a second loop formed of the first stent wire and defining a second loop opening, and (ii) the second stent wire passing through the second loop opening,
   wherein, in a view normal to a first plane containing the first loop and the second loop, the first double-loop structure further includes two intersection points formed by the first stent wire, where the first loop is between a first intersection point of the two intersection points and a second intersection point of the two intersection points, and the second loop is separated from the first loop by the second intersection point,
   wherein, in an axial direction of the stent device and relative to the first intersection point, the second loop opening is more distal than the first loop opening,
   wherein the first loop opening has a first length in the axial direction and the second loop opening has a second length in the axial direction, and the second length is greater than the first length,
   wherein the secondary interlocking structure includes the first stent wire and the second stent wire passing over each other, and
   wherein the first stent wire includes a first peak and a first valley and the first loop is located at the first peak or the first valley of the first stent wire.

2. The stent device according to claim 1, wherein the secondary interlocking structure does not include a loop.

3. The stent device according to claim 1, wherein, in the secondary interlocking structure, the first stent wire and the second stent wire pass over each without forming a loop.

4. The stent device according to claim 2, wherein the second stent wire includes a second peak and a second valley, wherein a portion of the first stent wire forming the secondary interlocking structure is the first peak, wherein a portion of the second stent wire forming the secondary interlocking structure is the second valley, and wherein, in the secondary interlocking structure, the first peak is located in the second valley.

5. The stent device according to claim 1, wherein a number of the primary interlocking structure is equal to or less than a number of the secondary interlocking structure.

6. The stent device according to claim 1, wherein the first peak and the first valley of the first stent wire are part of a pattern of alternating peaks and valleys along the first stent wire,
   wherein the first stent wire does not include three consecutive loops along the pattern of alternating peaks and valleys, and
   wherein the three consecutive loops include the first loop.

7. The stent device according to claim 1, wherein the first peak and the first valley of the first stent wire are part of a pattern of alternating peaks and valleys along the first stent wire, and
   wherein, among four consecutive alternating peaks and valleys in the pattern of alternating peaks and valleys, the first stent wire includes the first loop.

8. The stent device according to claim 1, wherein the first peak and the first valley of the first stent wire are part of a pattern of alternating peaks and valleys along the first stent wire, and
   wherein, among four consecutive alternating peaks and valleys in the pattern of alternating peaks and valleys, the first stent wire includes the first loop and a second loop.

9. A stent delivery system, including:
   the stent device according to claim 1;
   a tip;
   a sheath having a capability to carry the stent device; and
   a pusher for pushing out the stent device from the sheath.

10. The stent device according to claim 1, wherein, in a first direction along the first stent wire, the first stent wire forming the first loop and the second loop includes an outward wire section and an inward wire section, the outward wire section extending between a first point that is before the first intersection point and a second point that is past the second intersection point and the inward wire section extending from the second point to a third point that is past the first intersection point, and
   wherein the outward wire section is on the same side of the inward wire section in both the first intersection point and the second intersection point.

11. The stent device according to claim 10, wherein the primary interlocking structure prevents axial shortening of the stent device.

12. A stent delivery system, including:
   the stent device according to claim 10;

a tip;
a sheath having a capability to carry the stent device; and
a pusher for pushing out the stent device from the sheath.

13. The stent device according to claim 1, wherein, in a first direction along the first stent wire, the first stent wire forming the first loop and the second loop includes an outward wire section and an inward wire section, the outward wire section extending between a first point that is before the first intersection point and a second point that is past the second intersection point and the inward wire section extending from the second point to a third point that is past the first intersection point, and
wherein the outward wire section is on a first side of the inward wire section in the first intersection point and the outward wire section is on a second side of the inward wire section in the second intersection point, the first side different from the second side.

14. The stent device according to claim 13, wherein the primary interlocking structure prevents axial shortening of the stent device.

15. A stent delivery system, including:
the stent device according to claim 13;
a tip;
a sheath having a capability to carry the stent device; and
a pusher for pushing out the stent device from the sheath.

16. A stent device, comprising:
a first stent wire and a second stent wire forming a cylindrical stent body, wherein the cylindrical stent body encloses an interior void space and defines an inner luminal side of the stent body;
a primary interlocking structure; and
a secondary interlocking structure,
wherein the primary interlocking structure includes (i) a first double-loop structure including a first loop formed of the first stent wire and defining a first loop opening and a second loop formed of the first stent wire and defining a second loop opening, (ii) a second double-loop structure including a third loop formed of the second stent wire and defining a third loop opening and a fourth loop formed of the second stent wire and defining a fourth loop opening, and (iii) the fourth loop passes through the second loop opening,
wherein, in a view normal to a first plane containing the first loop and the second loop, the first double-loop structure further includes a first primary intersection point and a second primary intersection point that are each formed by the first stent wire, where the first loop is between the first primary intersection point and the second primary intersection point, and the second loop is separated from the first loop by the second primary intersection point,
wherein, in a view normal to a second plane containing the third loop and the fourth loop, the second double-loop structure further includes a third primary intersection point and a fourth primary intersection point that are each formed by the second stent wire, where the third loop is between the third primary intersection point and the fourth primary intersection point, and the fourth loop is separated from the third loop by the fourth primary intersection point,
wherein, in an axial direction of the stent device and relative to the first primary intersection point, the second loop opening is more distal than the first loop opening,
wherein the first loop opening has a first length in the axial direction and the second loop opening has a second length in the axial direction, and the second length is greater than the first length,
wherein, in the axial direction of the stent device and relative to the third primary intersection point, the fourth loop opening is more distal than the third loop opening,
wherein the secondary interlocking structure includes the first stent wire and the second stent wire passing over each other, and
wherein the first stent wire includes a first peak and a first valley and the first loop is located at the first peak or the first valley of the first stent wire.

17. The stent device according to claim 16, wherein the primary interlocking structure prevents axial shortening of the stent device.

18. A stent delivery system, including:
the stent device according to claim 16;
a tip;
a sheath having a capability to carry the stent device; and
a pusher for pushing out the stent device from the sheath.

19. A stent device, comprising:
a first stent wire and a second stent wire forming a cylindrical stent body, wherein the cylindrical stent body encloses an interior void space and defines an inner luminal side of the stent body;
a primary interlocking structure; and
a secondary interlocking structure,
wherein the primary interlocking structure includes (i) a first double-loop structure including a first loop formed of the first stent wire and defining a first loop opening having a first opening axis and a second loop formed of the first stent wire and defining a second loop opening having a second opening axis, and (ii) the second stent wire passing through the second loop opening,
wherein the first double-loop structure further includes a first primary intersection point and a second primary intersection point that are each formed by the first stent wire and, in a view in a direction of the second opening axis, a first imaginary line connects, in sequence, the first primary intersection point, the first opening axis, the second primary intersection point, and the second opening axis,
wherein, in an axial direction of the stent device and relative to the first primary intersection point, the second loop opening is more distal than the first loop opening,
wherein the first loop opening has a first length in the axial direction and the second loop opening has a second length in the axial direction, and the second length is greater than the first length,
wherein the secondary interlocking structure includes the first stent wire and the second stent wire passing over each other, and
wherein the first stent wire includes a first peak and a first valley and the first loop is located at the first peak or the first valley of the first stent wire.

20. The stent device according to claim 19, wherein the primary interlocking structure further includes (iii) a second double-loop structure including a third loop formed of the second stent wire and defining a third loop opening having a third opening axis and a fourth loop formed of the second stent wire and defining a fourth loop opening having a fourth opening axis,
wherein the second double-loop structure further includes a third primary intersection point and a fourth primary intersection point that are each formed by the second stent wire and, in a view in a direction of the fourth opening axis, a second imaginary line connects, in sequence, the third primary intersection point, the third opening axis, the fourth primary intersection point, and the fourth opening axis.

21. The stent device according to claim 20, wherein one of the third loop and the fourth loop passes through the second loop opening.

22. The stent device according to claim 20, wherein the fourth loop passes through the second loop opening.

23. The stent device according to claim 20, wherein the primary interlocking structure prevents axial shortening of the stent device.

24. A stent delivery system, including:
the stent device according to claim 20;
a tip;
a sheath having a capability to carry the stent device; and
a pusher for pushing out the stent device from the sheath.

25. The stent device according to claim 19, wherein a ratio of a number of the secondary interlocking structure to a number of the primary interlocking structure is 0.15 to 0.60.

26. The stent device according to claim 1, wherein a ratio of a number of the secondary interlocking structure to a number of the primary interlocking structure is 0.15 to 0.60.

27. The stent device according to claim 16, wherein a ratio of a number of the secondary interlocking structure to a number of the primary interlocking structure is 0.15 to 0.60.

* * * * *